(12) United States Patent
Locke et al.

(10) Patent No.: US 11,351,063 B2
(45) Date of Patent: Jun. 7, 2022

(54) COMPOSITE DRESSINGS FOR IMPROVED GRANULATION AND REDUCED MACERATION WITH NEGATIVE-PRESSURE TREATMENT

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 183 days.

(21) Appl. No.: 15/997,841

(22) Filed: Jun. 5, 2018

(65) Prior Publication Data
US 2018/0353339 A1 Dec. 13, 2018

Related U.S. Application Data

(60) Provisional application No. 62/565,754, filed on Sep. 29, 2017, provisional application No. 62/516,540, (Continued)

(51) Int. Cl.
*A61F 13/02* (2006.01)
*A61F 13/00* (2006.01)
*A61M 1/00* (2006.01)

(52) U.S. Cl.
CPC .... *A61F 13/0216* (2013.01); *A61F 13/00068* (2013.01); *A61F 13/0223* (2013.01); (Continued)

(58) Field of Classification Search
CPC ............ A61F 13/0216; A61F 13/00068; A61F 13/0223; A61F 13/0213; A61F 13/0206; (Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Law, K., Definitions for Hydrophilicity, Hydrophobicity, and Superhydrophobicity: Getting the Basics Right, J. Phys. Chem. Lett., 5, Feb. 20, 2014, pp. 686-688 (Year: 2014).*

(Continued)

*Primary Examiner* — Nicholas J. Weiss
*Assistant Examiner* — Alessandro R Del Priore

(57) ABSTRACT

A dressing for treating a tissue site with negative pressure may include a first layer having a first side, a second side, and fenestrations having a raised edge extending from the first side. The raised edge is configured to expand in response to a pressure gradient across the first layer. The dressing also includes a second layer adjacent to the first side. The second layer includes a manifold. The dressing also includes a cover coupled to the second layer opposite the first layer. The cover includes a polymer drape.

27 Claims, 14 Drawing Sheets

Related U.S. Application Data filed on Jun. 7, 2017, provisional application No. 62/516,550, filed on Jun. 7, 2017, provisional application No. 62/516,566, filed on Jun. 7, 2017.

(52) U.S. Cl.
CPC ............ *A61M 1/90* (2021.05); *A61F 13/0206* (2013.01); *A61F 13/0213* (2013.01)

(58) Field of Classification Search
CPC ........ A61F 2013/00536; A61F 13/0203; A61F 13/0226; A61F 2013/00863; A61F 13/00029; A61F 13/022; A61F 2013/00604; A61F 13/00021; A61F 13/025; A61F 13/512; A61F 2013/00255; A61F 2013/00638; A61F 2013/53081; A61M 1/0088; A61M 27/00; A61M 1/0058; A61M 1/0001; A61M 3/0283; A61B 46/00

See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A * | 11/1979 | Gallagher ................. B32B 5/18 5/500 |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Bustad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,983,173 A | 1/1991 | Patience et al. |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A * | 5/1994 | Karami ................. A61F 13/025 602/54 |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A * | 6/1997 | Fabo ................. A61F 13/0276 424/443 |
| 5,636,643 A | 6/1997 | Argenta et al. |
| 5,645,081 A | 7/1997 | Argenta et al. |
| 5,720,714 A | 2/1998 | Penrose |
| 5,842,503 A * | 12/1998 | Foley .................... F16K 15/147 454/162 |
| 5,951,505 A | 9/1999 | Gilman et al. |
| 5,981,822 A | 11/1999 | Addison |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,623,681 B1 | 9/2003 | Taguchi et al. |
| 6,653,523 B1 * | 11/2003 | McCormack ........... A61L 15/18 604/367 |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |

(56) References Cited

U.S. PATENT DOCUMENTS

| | | |
|---|---|---|
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1* | 2/2004 | Hunt ................. A61L 15/24 604/317 |
| 2004/0126413 A1* | 7/2004 | Sigurjonsson ........ A61L 15/425 424/445 |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2005/0226917 A1 | 10/2005 | Burton |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1 | 12/2008 | Olson et al. |
| 2009/0047495 A1 | 2/2009 | Hubbs |
| 2009/0082746 A1* | 3/2009 | Thomas ................ A61F 13/512 604/378 |
| 2009/0221979 A1 | 9/2009 | Huang et al. |
| 2009/0234307 A1 | 9/2009 | Vitaris |
| 2009/0293887 A1 | 12/2009 | Wilkes et al. |
| 2010/0030170 A1 | 2/2010 | Keller et al. |
| 2010/0030178 A1* | 2/2010 | MacMeccan ....... A61F 13/0213 604/378 |
| 2010/0036334 A1 | 2/2010 | Heagle et al. |
| 2010/0063484 A1* | 3/2010 | Heagle .................. A61M 37/00 604/355 |
| 2010/0069863 A1 | 3/2010 | Olson |
| 2010/0069885 A1 | 3/2010 | Stevenson et al. |
| 2010/0106115 A1 | 4/2010 | Hardman et al. |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0178451 A1 | 7/2011 | Robinson et al. |
| 2011/0213287 A1* | 9/2011 | Lattimore ............... A61M 1/90 604/319 |
| 2011/0224631 A1 | 9/2011 | Simmons et al. |
| 2011/0282309 A1 | 11/2011 | Adie et al. |
| 2011/0313374 A1 | 12/2011 | Lockwood et al. |
| 2012/0046603 A1 | 2/2012 | Vinton |
| 2012/0157945 A1 | 6/2012 | Robinson et al. |
| 2012/0209226 A1 | 8/2012 | Simmons et al. |
| 2012/0238932 A1 | 9/2012 | Atteia et al. |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1 | 2/2014 | Barberio |
| 2014/0058309 A1 | 2/2014 | Addison et al. |
| 2014/0081192 A1 | 3/2014 | Wenske et al. |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1* | 8/2014 | Von Wolff ............. A61L 15/52 156/244.11 |
| 2014/0350494 A1 | 11/2014 | Hartwell et al. |
| 2014/0364819 A1 | 12/2014 | VanDelden |
| 2015/0038933 A1 | 2/2015 | Day et al. |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0141941 A1 | 5/2015 | Allen et al. |
| 2015/0150729 A1 | 6/2015 | Dagger et al. |
| 2015/0174291 A1 | 6/2015 | Zimnitsky et al. |
| 2015/0174304 A1 | 6/2015 | Askem et al. |
| 2015/0290042 A1 | 10/2015 | Freer et al. |
| 2015/0290050 A1 | 10/2015 | Wada |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1 | 2/2016 | Hartwell et al. |
| 2016/0095754 A1 | 4/2016 | Andrews et al. |
| 2016/0144084 A1 | 5/2016 | Collinson et al. |
| 2016/0144085 A1 | 5/2016 | Melin et al. |
| 2016/0166744 A1 | 6/2016 | Hartwell |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |
| 2017/0079846 A1 | 3/2017 | Locke et al. |
| 2017/0095374 A1 | 4/2017 | Lauer |
| 2017/0143552 A1* | 5/2017 | Hartwell ............. A61F 13/0216 |
| 2017/0172807 A1 | 6/2017 | Robinson et al. |
| 2017/0174852 A1 | 6/2017 | Hanschen et al. |
| 2017/0209312 A1 | 7/2017 | Kanchagar et al. |
| 2017/0258640 A1 | 9/2017 | Ahsani Ghahreman et al. |
| 2017/0312406 A1 | 11/2017 | Svensby |
| 2017/0348154 A1 | 12/2017 | Robinson et al. |
| 2017/0348158 A1 | 12/2017 | You et al. |
| 2018/0071148 A1 | 3/2018 | Lockwood et al. |
| 2018/0289872 A1 | 10/2018 | Coulthard et al. |
| 2018/0296394 A1 | 10/2018 | Barberio |
| 2019/0184075 A1 | 6/2019 | Roos |

FOREIGN PATENT DOCUMENTS

| | | |
|---|---|---|
| AU | 755496 B2 | 12/2002 |
| CA | 2005436 A1 | 6/1990 |

(56) References Cited

FOREIGN PATENT DOCUMENTS

| | | |
|---|---|---|
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0174803 A2 | 3/1986 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2468905 A | 9/2010 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9319709 A1 | 10/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2007113597 A2 | 10/2007 |
| WO | 2010061228 A1 | 6/2010 |
| WO | 2011008497 A2 | 1/2011 |
| WO | 2011121127 A1 | 10/2011 |
| WO | 2011127188 A2 | 10/2011 |
| WO | 2011135286 A1 | 11/2011 |
| WO | 2014140608 A1 | 9/2014 |
| WO | 2015098373 A1 | 7/2015 |
| WO | 2015168681 A1 | 11/2015 |
| WO | 2015173547 A1 | 11/2015 |
| WO | 2015193257 A1 | 12/2015 |
| WO | 2016014645 A1 | 1/2016 |
| WO | 2016015001 A2 | 1/2016 |
| WO | 2017040045 A1 | 3/2017 |
| WO | 2017119996 A1 | 7/2017 |

OTHER PUBLICATIONS

Law, K., Definitions for Hydrophilicity, Hydrophobicity, and Superhydrophobicity: Getting the Basics Right, J. Phys. Chem. Lett., 5, Feb. 20, 2014, pp. 686-688 (Year: 2014).*

Office Action for related U.S. Appl. No. 16/000,284, dated Jun. 8, 2020.

Office Action for related U.S. Appl. No. 15/997,833, dated Jun. 19, 2020.

3M™ Medical Tape 9830, Single Sided Transparent Polyethylene, 63# Liner, Configurable. Retrieved on May 21, 2019. Retrieved from the Internet: <www.3m.com/3M/en_US/company-US/all-3m-products/~/3M-9830-Transparent-Polyethylene-Single-Sided-Medical-Tape-63-Liner/?N 5002385+8729793+3294739632&rt=rud; accessed May 21, 2019>.

3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-US/all-3m-products/~/3M-9948-Single-Sided-Themnoplastic-Elastomer-TPE-Medical-Incise-Tape/?N=5002385+4294834151&rt=d; accessed May 21, 2019>.

International Search Report and Written Opinion for related application PCT/US2018/036013, dated Aug. 7, 2018.

International Search Report and Written Opinion for related application PCT/US2018/035945, dated Aug. 24, 2018.

International Search Report and Written Opinion for related application PCT/US2018/036074, dated Aug. 24, 2018.

International Search Report and Written Opinion for related application PCT/US2018/035957, dated Sep. 28, 2018.

International Search Report and Written Opinion for related application PCT/US2018/035995, dated Oct. 1, 2018.

International Search Report and Written Opinion for related application PCT/US2018/036021, dated Aug. 24, 2018.

International Search Report and Written Opinion for related application PCT/US2018/036019, dated Oct. 18, 2018.

International Search Report and Written Opinion for related application PCT/US2018/036054, dated Aug. 24, 2018.

International Search Report and Written Opinion for related application PCT/US2018/036049, dated Aug. 29, 2018.

International Search Report and Written Opinion for related application PCT/US2018/036077, dated Aug. 24, 2018.

International Search Report and Written Opinion for related application PCT/US2018/036129, dated Oct. 8, 2018.

Heit, et al., "Foam Pore Size Is a Critical Interface Parameter of Suction-Based Wound Healing Devices," copyright 2012 by the American Society of Plastic Surgeons (www. PRSJournal.com) (Year: 2011).

Office Action for related U.S. Appl. No. 16/000,284, dated Sep. 23, 2019.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634 639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp : 66-70, and 9 page English translation thereof.

Yusupov. Yu.N., et al; "Active Wound Drainage", Vestnki Khirurgi, vol. 138, Issue 4, 1987, and 7 page English translation thereof.

(56) References Cited

OTHER PUBLICATIONS

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction Around drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Septembers, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.L Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties A Manual of Its Practical Application, (W.B. Saunders Co., Philadelphia, PA 1909), pp. 17-25, 44-64, 90-96, 167-170, and 210-211.
V.A. Solovev et al.. Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Office Action for related U.S. Appl. No. 15/997,809, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 16/000,368, dated Dec. 14, 2020.
Office Action for related U.S. Appl. No. 15/997,818, dated Jan. 27, 2021.
Office Action for related U.S. Appl. No. 15/997,809, dated Jan. 28, 2021.
Office Action for related U.S. Appl. No. 15/997,833, dated Mar. 26, 2021.
Office Action for related U.S. Appl. No. 16/000,215, dated Apr. 12, 2021.
Chinese Office Action for related application 2018800367248, dated Apr. 28, 2021.
Office Action for related U.S. Appl. No. 15/997,833, dated Jun. 7, 2021.
Chinese Office Action for related application 201880048393X, dated May 26, 2021.
Office Action for related U.S. Appl. No. 15/997,809, dated Jul. 8, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.

(56) References Cited

OTHER PUBLICATIONS

Office action for related U.S. Appl. No. 16/000,002, dated Oct. 4, 2021.
Office Action for related U.S. Appl. No. 15/997,923, dated Nov. 16, 2021.
Office Action for related U.S. Appl. No. 16/000,411, dated Jan. 31, 2022.
Office Action for related U.S. Appl. No. 16/959,651, dated Feb. 15, 2022.
Japanese Office Action for related application 2019-566886, dated Mar. 29, 2022.
Office Action for related U.S. Appl. No. 16/000,383, dated Mar. 31, 2022.
Pappas et al., "Wettability Tests of Polymer Films and Fabrics and Determination of Their Surface Energy by Contact-Angle Methods," Army Research Laboratory, ARL-TR-4056, Mar. 2007, p. 5.
Baltex, Technical Fabrics & Technical Textile Products, https://www.baltex.co.uk/products/xd-spacer-fabrics/, accessed Apr. 20, 2022.
Yimin Qin, Applications of Advanced Technologies in the Development of Functional Medical Textile Materials, Medical Textile Materials, 2016, pp. 55-70, Woodhead Publishing.
Baltex, Technical Fabrics & Technical Textile Products http://web.archive.org/web/20150118084138/http://www.baltex.co.uk/products/Healthcarefabrics/, 2015.
Office Action for related U.S. Appl. No. 17/204,548, dated Apr. 19, 2022.

* cited by examiner

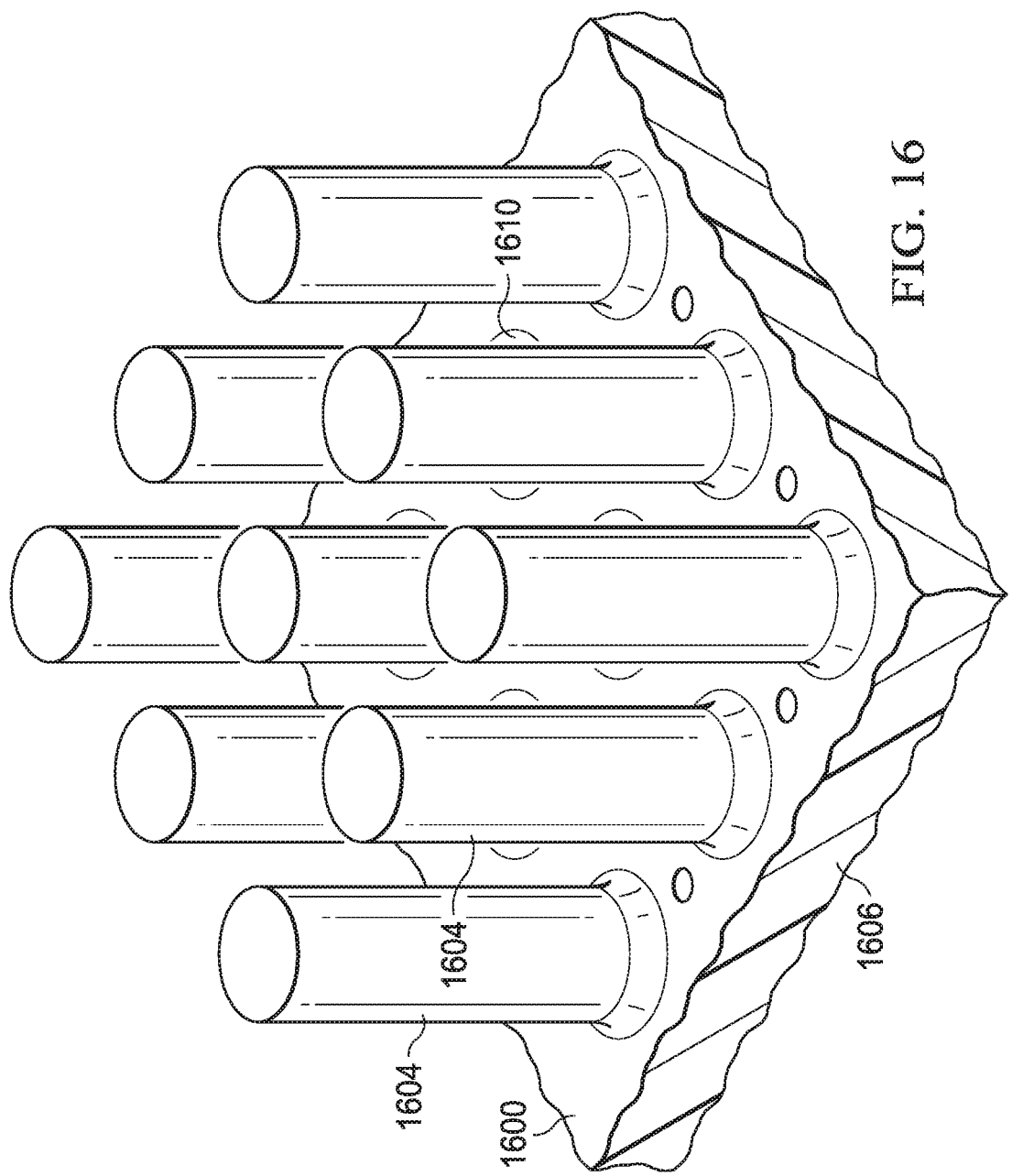

COMPOSITE DRESSINGS FOR IMPROVED GRANULATION AND REDUCED MACERATION WITH NEGATIVE-PRESSURE TREATMENT

RELATED APPLICATION

This application claims the benefit, under 35 U.S.C. § 119(e), of the filing of U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be a composite of dressing layers, including a release film, a perforated polymer film, open-cell foam, and an adhesive drape. Some dressings may also include a bonded silicone having perforations. The perforation pattern of the polymer film can be aligned with the perforation pattern of at least a central area of the silicone. In some embodiments, the perforations may be slits or slots. In some embodiments, the perforations may include fenestrations having a raised edge extending from a first side of the polymer film. The polymer film may be hydrophobic and may have a contact angle with water greater than 90 degrees. The polymer film may comprise or consist of a polyethylene film or an ethyl methyl acrylate film. The polymer film may have an area density of less than 30 grams per square meter. The open-cell foam may be reticulated foam in some examples, and may be relatively thin and hydrophobic to reduce the fluid hold capacity of the dressing. The foam may also be thin to reduce the dressing profile and increase flexibility, which can enable it to conform to wound beds and other tissue sites under negative pressure. In some embodiments, the polymer film is welded to the foam using heat, radio frequency welding, or method to generate heat, such as ultrasonic.

In some embodiments, a dressing for treating a tissue site with negative pressure may include a first layer having a first side, a second side, and fenestrations having a raised edge extending from the first side, the raised edge configured to expand in response to a pressure gradient across the first layer; a second layer adjacent to the first side, the second layer comprising a manifold; and a cover coupled to the second layer opposite the first layer, the cover comprising a polymer drape.

In some embodiments, a dressing for treating a tissue site with negative pressure may include a first layer comprising a film having perforations and fenestrations through the film that are configured to expand in response to a pressure gradient across the film; a second layer adjacent to the first layer, the second layer comprising a manifold; and a cover adjacent to the second layer opposite the first layer.

In some embodiments, a dressing for treating a tissue site with negative pressure may include a fluid control layer comprising fluid restrictions that are elastomeric and configured to be responsive to a pressure gradient across the fluid control layer; a manifold layer adjacent to the fluid control layer; a cover adjacent to the manifold layer opposite the fluid control layer; and a sealing layer adjacent to the fluid control layer opposite the manifold layer. The sealing layer may include apertures aligned with the fluid restrictions. The fluid control layer and the sealing layer may each have a contact angle with water of at least 70 degrees. The fluid control layer and the sealing layer may be each less than 100 microns thick. The fluid control layer and the sealing layer may have a hardness in a range of 20 Shore A to 90 Shore A.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 16 illustrates another example manifold that may be associated with some embodiments of the dressing of FIG. 1.

DESCRIPTION OF EXAMPLE EMBODIMENTS

The following description of example embodiments provides information that enables a person skilled in the art to make and use the subject matter set forth in the appended claims, and may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
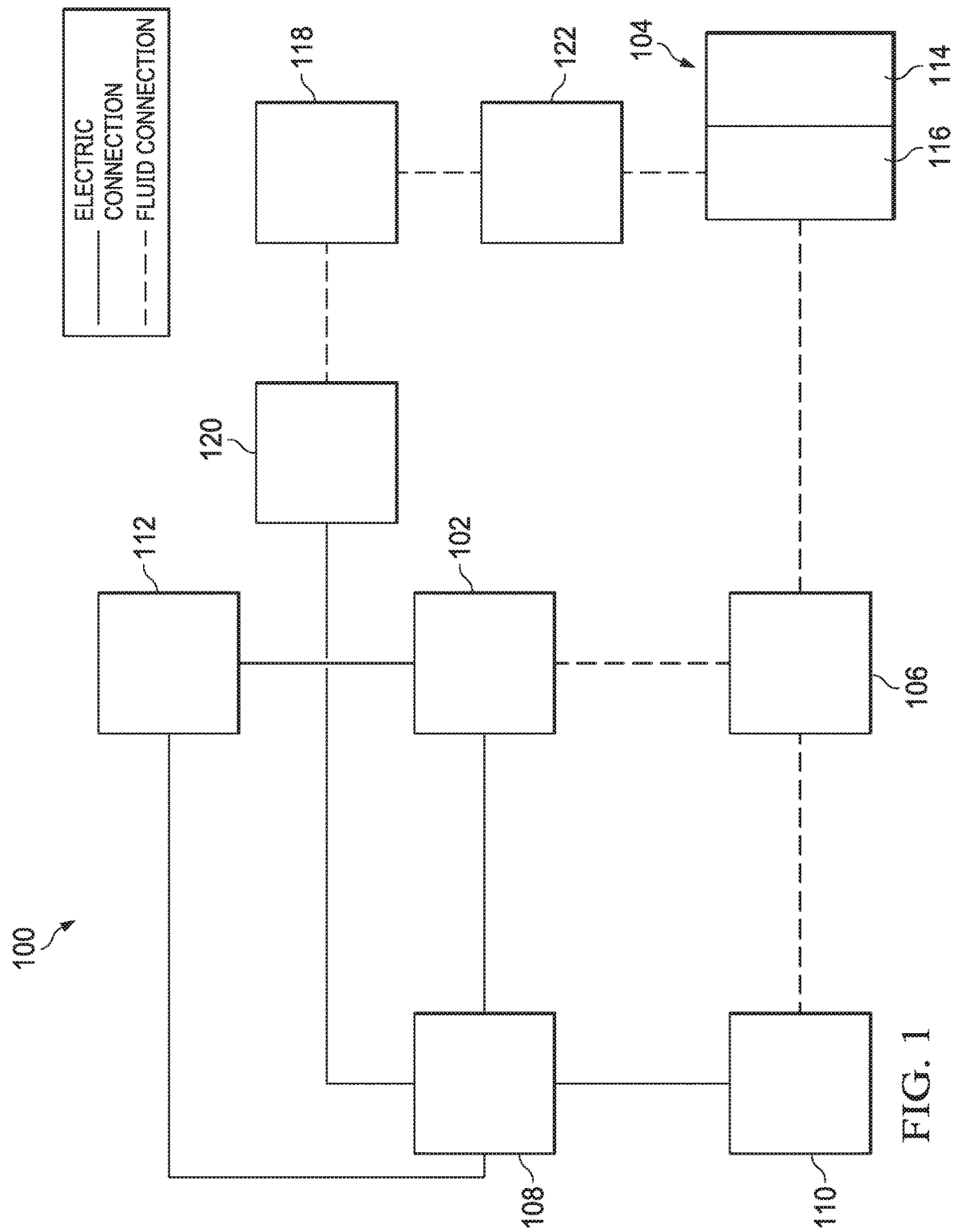
FIG. 1 is a functional block diagram of an example embodiment of a therapy system that can provide tissue treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a first sensor 110 and a second sensor 112 coupled to the controller 108. As illustrated in the example of FIG. 1, the dressing 104 may comprise or consist essentially of one or more dressing layers, such as a tissue interface 114, a cover 116 (or drape), or both in some embodiments.

The therapy system 100 may also include a source of instillation solution, such as saline, for example. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108 and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108. The negative-pressure source maybe fluidly coupled to one or more distribution components, which provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components, including sensors and data communication devices. In some embodiments, for example, a dressing interface may facilitate coupling a fluid conductor to the dressing 104. For example, such a dressing interface may be a SENSA-T.R.A.C.™ Pad available from KCI of San Antonio, Tex.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudate and other fluid withdrawn from a tissue site. In many environments, a rigid container may be preferred or required for collecting, storing, and disposing of fluid. In other environments, fluid may be properly disposed of without rigid container storage, and a re-usable container could reduce waste and costs associated with negative-pressure therapy. Additionally or alternatively, an absorbent may be integrated with the dressing 104 to manage fluid withdrawn from a tissue site.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the first sensor 110 and the second sensor 112, are generally known in the art as any apparatus operable to detect or measure a physical phenomenon or property, and generally provide a signal indicative of the phenomenon or property that is detected or measured. For example, the first sensor 110 and the second sensor 112 may be configured to measure one or more operating parameters of the therapy system 100. In some embodiments, the first sensor 110 may be a transducer configured to measure pressure in a pneumatic pathway and convert the measurement to a signal indicative of the pressure measured. In some embodiments, for example, the first sensor 110 may be a piezo-resistive strain gauge. The second sensor 112 may optionally measure operating parameters of the negative-pressure source 102, such as the voltage or current, in some embodiments. Preferably, the signals from the first sensor 110 and the second sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms and have more than one layer in some embodiments. The tissue interface 114 may also have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, Calif.; polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site, such as a surface wound. In some embodiments, for example, some or all of the cover 116 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flows toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
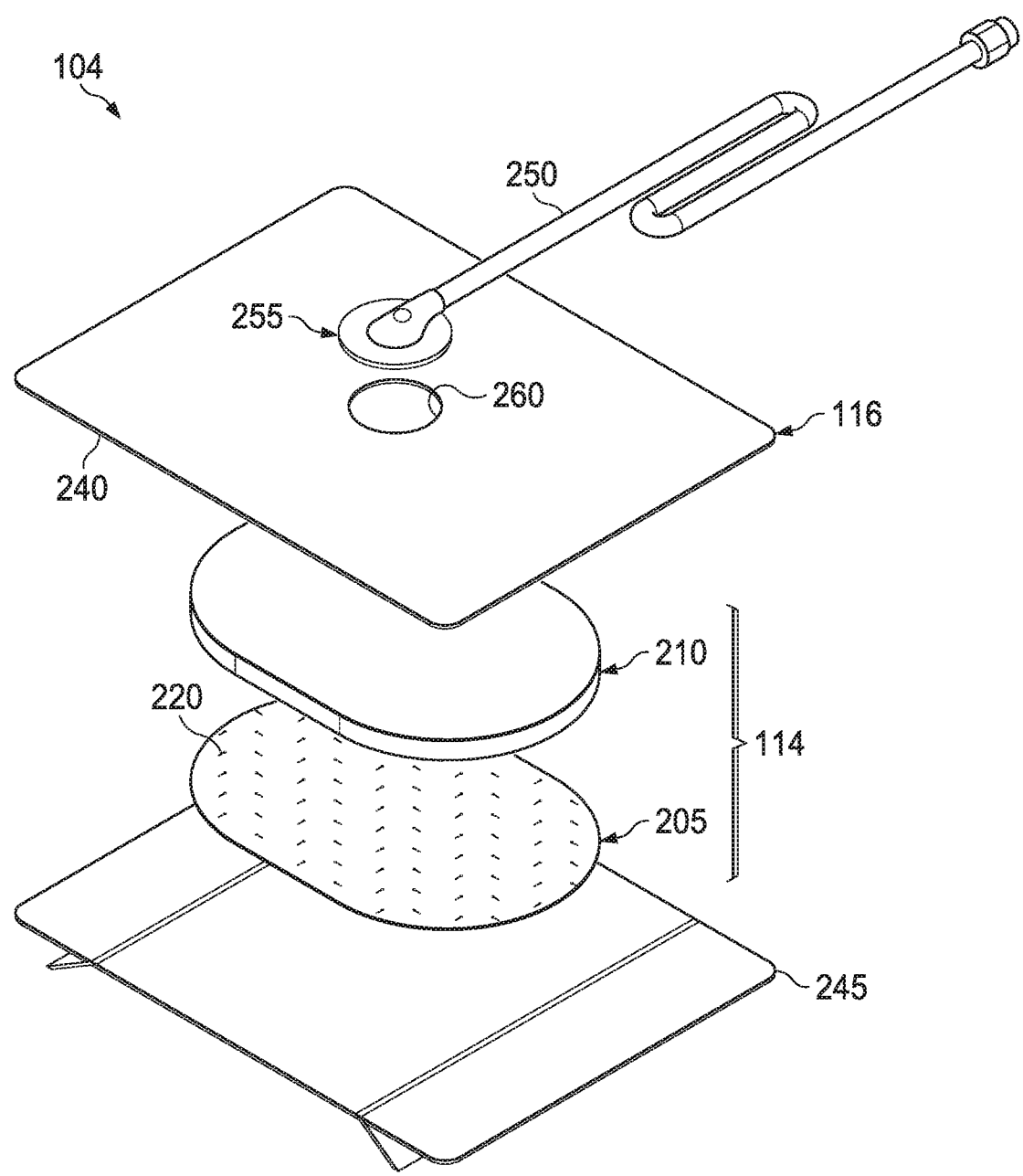
FIG. 2 is an assembly view of an example of a dressing, illustrating additional details that may be associated with some example embodiments of the therapy system of FIG. 1.

FIG. 2 is an assembly view of an example of the dressing 104 of FIG. 1, illustrating additional details that may be associated with some embodiments in which the tissue interface 114 comprises more than one layer. In the example of FIG. 2, the tissue interface 114 comprises a first layer 205 and a second layer 210. In some embodiments, the first layer 205 has a first side and a second side. The second layer 210 may be adjacent the first side of the first layer 205. For example, the first layer 205 and the second layer 210 may be stacked so that the first layer 205 is in contact with the second layer 210. The first layer 205 may also be bonded or welded to the second layer 210 in some embodiments.

The first layer 205 may comprise or consist essentially of a means for controlling or managing fluid flow. In some embodiments, the first layer 205 may comprise or consist essentially of an elastomeric material that is impermeable to liquid. For example, the first layer 205 may comprise or consist essentially of a polymer film. The first layer 205 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited. For example, the surface of the first layer 205 may have a substantially flat surface, with height variations limited to 0.2 millimeters over a centimeter.

In some embodiments, the first layer 205 may be hydrophobic, and may be more hydrophobic than the second layer 210. The hydrophobicity of the first layer 205 may vary, but may have a contact angle with water of at least 90 degrees in some embodiments. In some embodiments the first layer 205 may have a contact angle with water of no more than 150 degrees. For example, in some embodiments, the contact angle of the first layer 205 may be in a range of at least 70 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the first layer 205 may be further enhanced with a hydrophobic coating of other materials, such as silicones and fluorocarbons, either as coated from a liquid, or plasma coated.

The area density of the first layer 205 may vary according to a prescribed therapy or application. In some embodiments, an area density of less than 40 grams per square meter may be suitable, and an area density of about 20-30 grams per square meter may be particularly advantageous for some applications.

In some embodiments, for example, the first layer 205 may comprise or consist essentially of a hydrophobic polymer, such as a polyethylene film or ethyl methyl acrylate (EMA). The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. The films may have a flexibility of 20 Shore A to 90 Shore A.

The first layer 205 may also be suitable for welding to other layers, including the second layer 210. For example, the first layer 205 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

In some embodiments, the first layer 205 may include a polymer film of polylactic acid, carboxymethyl cellulose, or polycaprolactone. In other embodiments, the first layer 205 may include a film of xanthan gum mixed with at least one of collagen, oxidized regenerated cellulose, and alginate. In some embodiments, the first layer 205 includes a film of xanthan gum and citric acid mixed with at least one of collagen, oxidized regenerated cellulose, and alginate. The first layer 205 may include a film co-polymerized with dialkylcarbamoylchloride in some embodiments.

In some embodiments, the first layer 205 may be a film coated with petrolatum gel. The petrolatum gel may have a viscosity of at least 10000 millipascal seconds. In some embodiments, the petrolatum gel has anti-microbial compounds.

In some embodiments, instead of silicone and polyethylene films, the first layer 205 may include long residency bio-resorbably polymer film formed from polylactic acid, carboxymethylcellulose, polycaprolactone, or other polymers that are able to be cross-linked, such that function is retained for greater than about 7 days and resorption occurs in greater than 12 days. In other embodiments, the first layer may include highly cross-linked bioipolymers such as collagen or alginate, which are mixed with xanthan gum in a ratio of 20% gum to biologic, and which is plasma treated to achieve a hydrophobic in a desired ranged. The film may also include citric acid to assist with biofilm reduction and limit concerns with bacterial build-up. In some embodiments, the film is formed of polyethylene, polyurethane, EMA, or biopolymers incorporating a texture, such as "Sharklet" that assists with the reduction of biofilm formation on the dressing. In other embodiments, the film is co-polymerized with dialkylcarbamoylchloride, which is highly hydrophobic, and may aid in preventing biofilm and bacterial attachment.

As illustrated in the example of FIG. 2, the first layer 205 may have one or more fluid restrictions 220, which can be distributed uniformly or randomly across the first layer 205, and can restrict fluid transfer across or through the first layer. The fluid restrictions 220 may be bi-directional and pressure-responsive. For example, each of the fluid restrictions 220 generally may comprise or consist essentially of an elastic passage that is normally unstrained to substantially reduce liquid flow, and can expand or open in response to a pressure gradient. In some embodiments, the fluid restrictions 220 may comprise or consist essentially of perforations in the first layer 205. Perforations may be formed by removing material from the first layer 205. For example, perforations may be formed by cutting through the first layer 205, which may also deform the edges of the perforations in some embodiments. The perforations may be able 3 mm long and about 0.8 mm wide in some embodiments. In the absence of a pressure gradient across the perforations, the passages may be sufficiently small to form a seal or fluid restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the first layer 205 may be a suitable valve for some applications. Fenestrations may also be formed by removing material from the first layer 205, but the amount of material removed and the resulting dimensions of the fenestrations may be up to an order of magnitude less than perforations, and may not deform the edges.

For example, some embodiments of the fluid restrictions 220 may comprise or consist essentially of one or more fenestrations, perforations, or combinations of fenestrations and perforations in the first layer 205. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The second layer 210 generally comprises or consists essentially of a manifold or a manifold layer, which provides a means for collecting or distributing fluid across the tissue interface 114 under pressure. For example, the second layer 210 may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 114.

In some illustrative embodiments, the pathways of the second layer 210 may be interconnected to improve distribution or collection of fluids. In some illustrative embodiments, the second layer 210 may comprise or consist essentially of a porous material having interconnected fluid pathways. For example, open-cell foam, porous tissue collections, and other porous material such as gauze or felted foam generally include pores, edges, and/or walls adapted to form interconnected fluid channels. Other suitable materials may include a 3D textile (Baltex, Muller, Heathcoates), non-woven (Libeltex, Freudenberg), a 3D polymeric structure (molded polymers, embossed and formed films, and fusion bonded films [Supracore]), and mesh, for example. Liquids, gels, and other foams may also include or be cured to include apertures and fluid pathways. In some embodiments, the second layer 210 may additionally or alternatively comprise projections that form interconnected fluid pathways. For example, the second layer 210 may be molded to provide surface projections that define interconnected fluid pathways. Any or all of the surfaces of the second layer 210 may have an uneven, coarse, or jagged profile In some embodiments, the second layer 210 may comprise or consist essentially of reticulated foam having pore sizes and free volume that may vary according to needs of a prescribed therapy. For example, reticulated foam having a free volume of at least 90% may be suitable for many therapy applications, and a foam having an average pore size in a range of 400-600 microns may be particularly suitable for some types of therapy. The tensile strength of the second layer 210 may also vary according to needs of a prescribed therapy. For example, the tensile strength of foam may be increased for instillation of topical treatment solutions. The 25% compression load deflection of the second layer 210 may be at least 0.35 pounds per square inch, and the 65% compression load deflection may be at least 0.43 pounds per square inch. In some embodiments, the tensile strength of the second layer 210 may be at least 10 pounds per square inch. The second layer 210 may have a tear strength of at least 2.5 pounds per inch. In some embodiments, the second layer 210 may be foam comprised of polyols such as polyester or polyether, isocyanate such as toluene diisocyanate, and polymerization modifiers such as amines and tin compounds. In one non-limiting example, the second layer 210 may be a reticulated polyurethane foam such as used in GRANUFOAM™ dressing or V.A.C. VERAFLO™ dressing, both available from KCI of San Antonio, Tex.

In some embodiments, the second layer 210 may be hydrophobic to minimize retention or storage of liquid in the dressing 104. In other embodiments, the second layer 210 may be hydrophilic. In an example in which the second layer 210 may be hydrophilic, the second layer 210 may also wick fluid away from a tissue site, while continuing to distribute negative pressure to the tissue site. The wicking properties of the second layer 210 may draw fluid away from a tissue site by capillary flow or other wicking mechanisms, for example. An example of a hydrophilic second layer 210 is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

In some embodiments, the second layer 210 may additionally or alternatively comprise or consist essentially of a polymer mesh. The polymer mesh may have an open area of at least 70%. In some embodiments, multiple layers of polymer mesh may be included, such that a tortuous path is formed. Additionally or alternatively, the second layer 210 may comprise or consist essentially of a flocked layer, such as a film or other suitable substrate flocked with fibers. A length of about 0.5 mm to about 6.0 mm may be suitable for some embodiments of the fibers. In some embodiments, the second layer 210 may additionally or alternatively comprise or consist essentially of a perforated cellulose mat or construction of layers of perforated mat. The perforations may be continuous or discontinuous through the structure, and when more than one layer is included, the layers may incorporate films to control flow direction. For example, cellulose may be treated to make the material hydrophobic, and the tissue interface may be perforated after adherence to a mat. Additionally or alternatively, the second layer 210 may comprise or consist essentially of a layered structure of sheets of hydrofiber material, which may be stitched together to form a mat. The stitching may assist with pressure and fluid communication. The stitched structure may be inter-spaced or replaced with a foamed version of this material, formed by means such as freeze drying, adding foaming agents, or by gas injection under high pressure during manufacture.

In other embodiments, the second layer 210 may include layers of bonded non-woven materials that can be plasma treated to create a desired level of hydrophobicity. In some embodiments, the second layer 210 may include one or more layers of closed cell foam, which can be perforated to enable manifolding of fluids and pressure. The one or more layers may include a foam with aligned or non-aligned vertical and horizontal perforations, such that manifolding occurs. In some embodiments, the manifold layer is formed from a flocked body. For example, a film may be coated with flocked fibers having a length of about 0.5 mm to about 6.0 mm. The film substrate may be perforated or slit, and the flocked fibers can function as a manifold and face away from the first layer 205. Alternatively, the flocked fibers can face towards the first layer 205. In some embodiments, the second layer 210 may include felted polyurethane foam having open cells and a thickness in a range of about 2 mm to about 5 mm. The felted polyurethane foam may have perforations therethrough in some embodiments.

The second layer 210 generally has a first planar surface and a second planar surface opposite the first planar surface. The thickness of the second layer 210 between the first planar surface and the second planar surface may also vary according to needs of a prescribed therapy. For example, the thickness of the second layer 210 may be decreased to relieve stress on other layers and to reduce tension on peripheral tissue. The thickness of the second layer 210 can also affect the conformability of the second layer 210. In some embodiments, a thickness in a range of about 5 millimeters to 10 millimeters may be suitable.

In the example of FIG. 2, the dressing 104 may further include an attachment device, such as an adhesive 240. The adhesive 240 may be, for example, a medically-acceptable, pressure-sensitive adhesive that extends about a periphery, a portion, or the entire cover 116. In some embodiments, for example, the adhesive 240 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 240 may be continuous or discontinuous. Discontinuities in the adhesive 240 may be provided by apertures or holes (not shown) in the adhesive 240. The apertures or holes in the adhesive 240 may be formed after application of the adhesive 240 or by coating the adhesive 240 in patterns on a carrier layer, such as, for example, a side of the cover 116. Apertures or holes in the adhesive 240 may also be sized to enhance the MVTR of the dressing 104 in some example embodiments.

As illustrated in the example of FIG. 2, in some embodiments, the dressing 104 may include a release liner 245 to protect the adhesive 240 prior to use. The release liner 245 may also provide stiffness to assist with, for example, deployment of the dressing 104. The release liner 245 may be, for example, a casting paper, a film, or polyethylene. Further, in some embodiments, the release liner 245 may be a polyester material such as polyethylene terephthalate (PET), or similar polar semi-crystalline polymer. The use of a polar semi-crystalline polymer for the release liner 245 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. Further, a release agent may be disposed on a side of the release liner 245 that is configured to contact the first layer 205. For example, the release agent may be a silicone coating and may have a release factor suitable to facilitate removal of the release liner 245 by hand and without damaging or deforming the dressing 104. In some embodiments, the release agent may be a fluorocarbon or a fluorosilicone, for example. In other embodiments, the release liner 245 may be uncoated or otherwise used without a release agent.

FIG. 2 also illustrates one example of a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114.

One or more of the components of the dressing 104 may additionally be treated with an antimicrobial agent in some embodiments. For example, the second layer 210 may be foam, mesh, or non-woven coated with an antimicrobial agent. In some embodiments, the first layer may comprise antimicrobial elements, such as fibers coated with an antimicrobial agent. Additionally or alternatively, some embodiments of the first layer 205 may be polymer coated or mixed with an antimicrobial agent. In other examples, the fluid conductor 250 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the second layer 210 may be a foam coated with such a mixture.

Individual components of the dressing 104 may be bonded or otherwise secured to one another with a solvent or non-solvent adhesive, or with thermal welding, for example, without adversely affecting fluid management.

Figure 3:
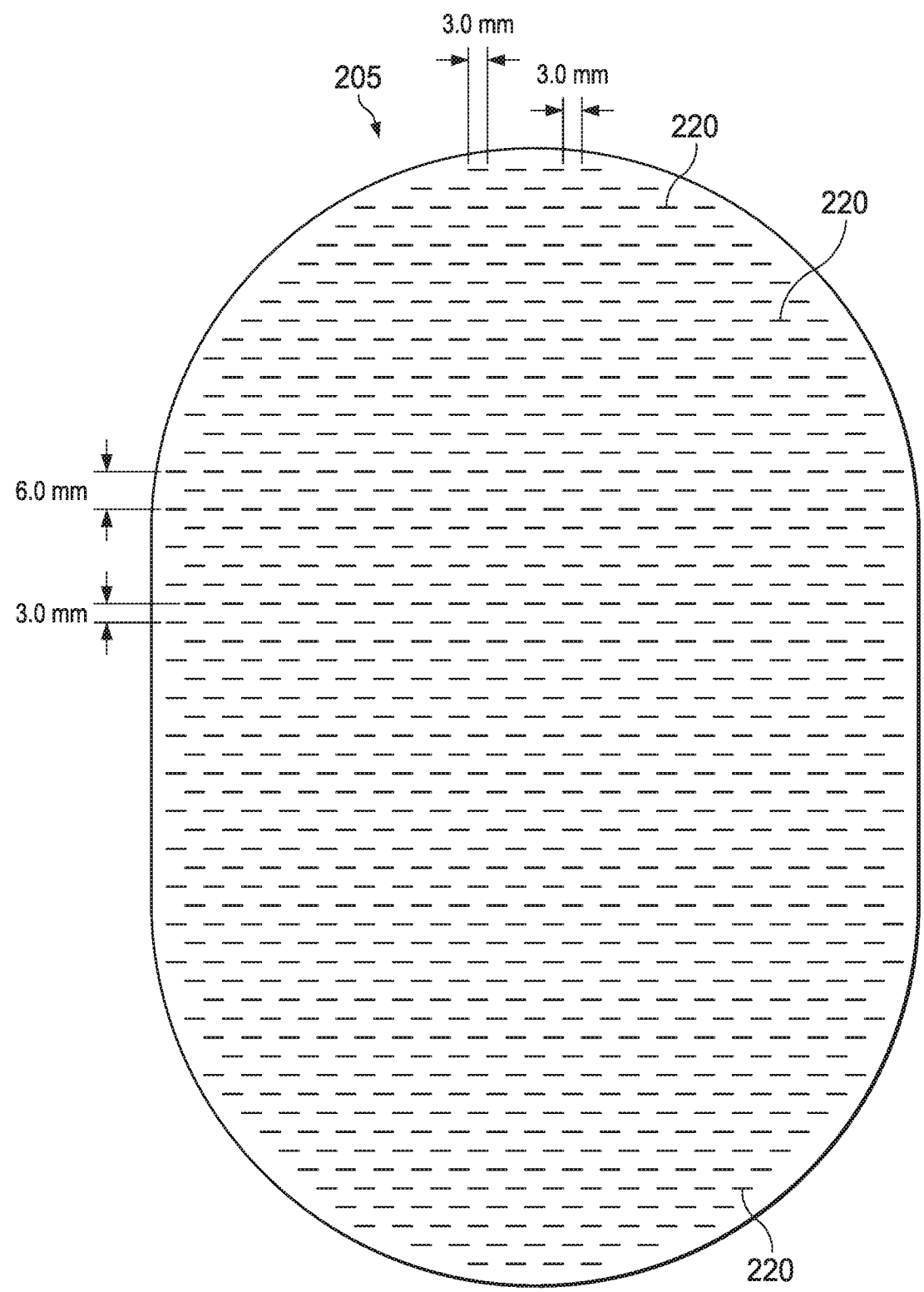
FIG. 3 is a schematic view of an example configuration of fluid restrictions in a layer that may be associated with some embodiments of the dressing of FIG. 2.

FIG. 3 is a schematic view of an example of the first layer 205, illustrating additional details that may be associated with some embodiments. As illustrated in the example of FIG. 3, the fluid restrictions 220 may each consist essentially of one or more linear fenestrations or perforations having a length of about 3 millimeters. FIG. 3 additionally illustrates an example of a uniform distribution pattern of the fluid restrictions 220. In FIG. 3, the fluid restrictions 220 are substantially coextensive with the first layer 205, and are distributed across the first layer 205 in a grid of parallel rows and columns, in which the fluid restrictions 220 are also mutually parallel to each other. In some embodiments, the rows may be spaced about 3 millimeters on center, and the fluid restrictions 220 within each of the rows may be spaced about 3 millimeters on center as illustrated in the example of FIG. 3. The fluid restrictions 220 in adjacent rows may be aligned or offset. For example, adjacent rows may be offset, as illustrated in FIG. 3, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

Figure 4:
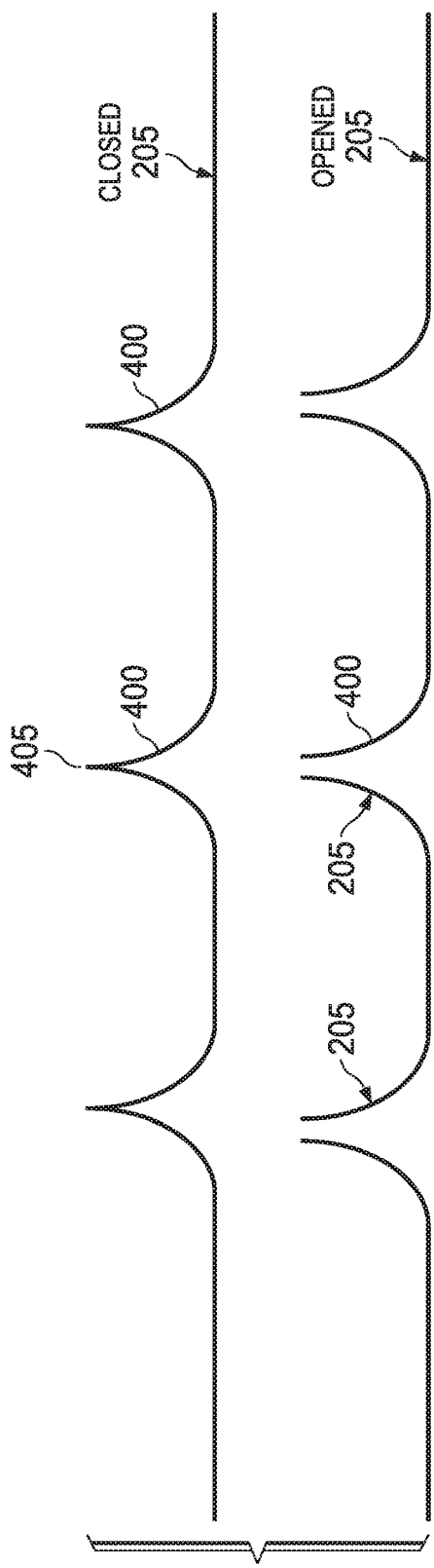
FIG. 4 is a detail view of example fluid restrictions in a closed state and open state, illustrating additional details that may be associated with some embodiments of the dressing of FIG. 2.

FIG. 4 is a side view of an example of the first layer 205, illustrating additional details that may be associated with some embodiments of the fluid restrictions 220. As shown, the fluid restrictions 220 may be fenestrations cut through the first layer 205, which may cause local deformation of the first layer 205 around the fluid restrictions 220. For example, the fluid restrictions 220 may have raised edges 405. The shape factor of the deformation can present an asymmetry to the fluid restrictions 220. At rest, as in the top illustration of FIG. 4, the raised edges 405 may be collapsed onto each other. A pressure gradient across the fluid restrictions 220 can separate the raised edges 405, as shown in the bottom illustration of FIG. 4. The asymmetry can allow fluid movement more easily in one direction than in another direction, and the fluid restrictions 220 can act as check valve, and more particularly, a duckbill valve. Thus, the fluid restrictions 220 can restrict liquid transfer across the first layer 205 from the first side to the second side.

Figure 5:
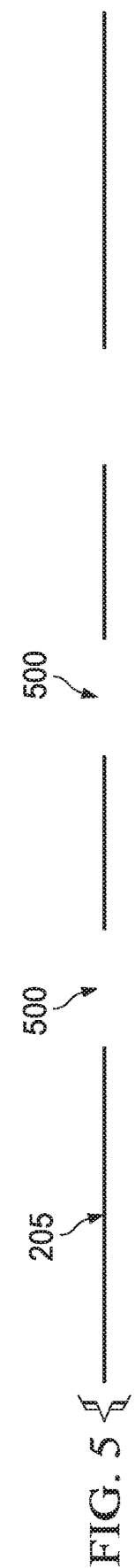
FIG. 5 is a detail view of other example fluid restrictions that may be associated with some embodiments of the dressing of FIG. 2.

FIG. 5 is a side view of another example configuration of the fluid restrictions 220, illustrating additional details that may be associated with some embodiments of the first layer 205. In FIG. 5, the fluid restrictions 220 comprise perforations (or slots), which may be linear perforations formed by the removal of material. For example, each of the fluid restrictions 220 may be holes 500 having a length of about 3.0 mm and a width of about 0.8 mm.

Figure 6:
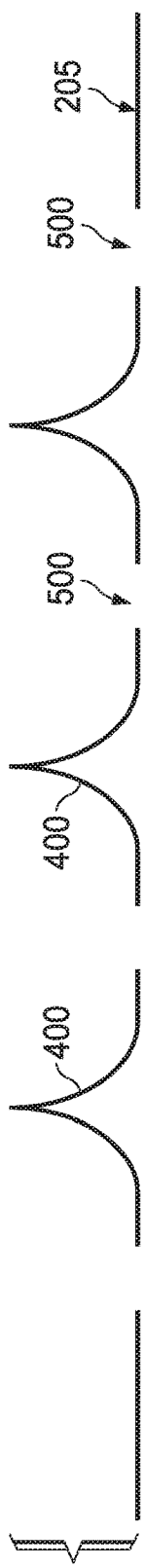
FIG. 6 is a detail view of other example fluid restrictions that may be associated with some embodiments of the dressing of FIG. 2.

FIG. 6 is a side view of another example configuration of the fluid restrictions 220, illustrating additional details that may be associated with some embodiments of the first layer 205. In FIG. 6, the fluid restrictions 220 include a combination of fenestrations having raised edges 405 and perforations having holes 500.

In some embodiments, a central zone of the first layer 205 may include a higher proportion of perforations than fenestrations. The central zone may cover about 50% of the area of the first layer 205, and the central zone may be coextensive with about 50% of a manifolding area. The peripheral zone may be coextensive with about 50% of the manifolding area. A ratio of perforations to fenestrations in the central zone of the first layer 205 may be greater than about 1:1. For example, the central zone of the first layer 205 may have a ratio of perforations to fenestrations of about 8:2. The peripheral zone, which may be about 50% of the available manifolding area, may have a perforation to fenestration ratio of about 2:8. In other embodiments, the first layer 205 may include two or more zones, and a ratio of the perforations to the fenestrations in a first zone may be about 8:2, while a ratio of the perforations to the fenestrations in a second zone may be about 2:8.

Different shaped perforations and fenestrations may be used in some embodiments. For example, the perforations may be circular, linear, or ovals. In some embodiments, the fenestrations may be formed from serrated or saw tooth forms. The saw tooth forms may show less resistance to fluid flow due to easier opening ability thereby enabling a higher flow rate or the ability to handle higher viscosity fluids.

The cover 116, the second layer 210, and the first layer 205, or various combinations may be assembled before application or in situ. For example, the cover 116 may be laminated to the second layer 210, and the first layer 205 may be laminated to the second layer 210 opposite the cover 116 in some embodiments. The first layer 205 may provide a smooth surface opposite the second layer 210. In some embodiments, one or more layers of the tissue interface 114 may coextensive. For example, the first layer 205 may be cut flush with the edge of the second layer 210, exposing the edge of the second layer 210, as illustrated in the embodiment of FIG. 2. In other embodiments, the first layer 205 may overlap the edge of the second layer 210. In some embodiments, the dressing 104 may be provided as a single, composite dressing. For example, the first layer 205 may be coupled to the cover 116 to enclose the second layer 210, wherein the first layer 205 is configured to face a tissue site.

In use, the release liner 245 (if included) may be removed to expose the first layer 205, which may be placed within, over, on, or otherwise proximate to a tissue site, particularly a surface tissue site and adjacent epidermis. The first layer 205 may be interposed between the second layer 210 and the tissue site and adjacent epidermis, which can substantially reduce or eliminate adverse interaction with the second layer 210. For example, the first layer 205 may be placed over a surface wound (including edges of the wound) and undamaged epidermis to prevent direct contact with the second layer 210. Treatment of a surface wound or placement of the dressing 104 on a surface wound includes placing the dressing 104 immediately adjacent to the surface of the body or extending over at least a portion of the surface of the body. Treatment of a surface wound does not include placing the dressing 104 wholly within the body or wholly under the surface of the body, such as placing a dressing within an abdominal cavity. The cover 116 may be sealed to an attachment surface, such as epidermis peripheral to a tissue site, around the second layer 210 and the first layer 205.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the first layer 205 to enhance the movement and proliferation of epithelial cells at a tissue site and reduce the likelihood of granulation tissue in-growth.

Thus, the dressing 104 can provide a sealed therapeutic environment proximate to a tissue site, substantially isolated from the external environment, and the negative-pressure source 102 can reduce the pressure in the sealed therapeutic environment. Negative pressure in the sealed environment may compress the second layer 210 into the first layer 205, which can deform the surface of the first layer 205 to provide an uneven, coarse, or jagged profile that can induce macrostrain and micro-strain in the tissue site in some embodiments. Negative pressure applied through the tissue interface 114 can also create a negative pressure differential across the fluid restrictions 220 in the first layer 205, which can open the fluid restrictions 220 to allow exudate and other liquid movement through the fluid restrictions 220 into the second layer 210 and the container 106. For example, in some embodiments in which the fluid restrictions 220 may comprise perforations through the first layer 205, a pressure gradient across the perforations can strain the adjacent material of the first layer 205 and increase the dimensions of the perforations to allow liquid movement through them, similar to the operation of a duckbill valve.

If the negative-pressure source 102 is removed or turned-off, the pressure differential across the fluid restrictions 220 can dissipate, allowing the fluid restrictions 220 to return to an unstrained or resting state and prevent or reduce the return rate of exudate or other liquid moving to the tissue site through the first layer 205.

In some applications, a filler may also be disposed between a tissue site and the first layer 205. For example, if the tissue site is a surface wound, a wound filler may be applied interior to the periwound, and the first layer 205 may be disposed over the periwound and the wound filler. In some embodiments, the filler may be a manifold, such as an open-cell foam. The filler may comprise or consist essentially of the same material as the second layer 210 in some embodiments.

Additionally or alternatively, the tissue interface 114 may be formed into strips suitable for use as bridges or to fill tunnel wounds, for example. Strips having a width of about 5 millimeters to 30 millimeters may be suitable for some embodiments.

Additionally or alternatively, the first layer 205 may comprise reinforcing fibers to increase its tensile strength, which may be advantageous for use in tunnel wounds.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the first layer 205, which can open or expand the fluid restrictions 220 from their resting state to allow the instillation solution or other fluid to be distributed to the tissue site.

Figure 7:
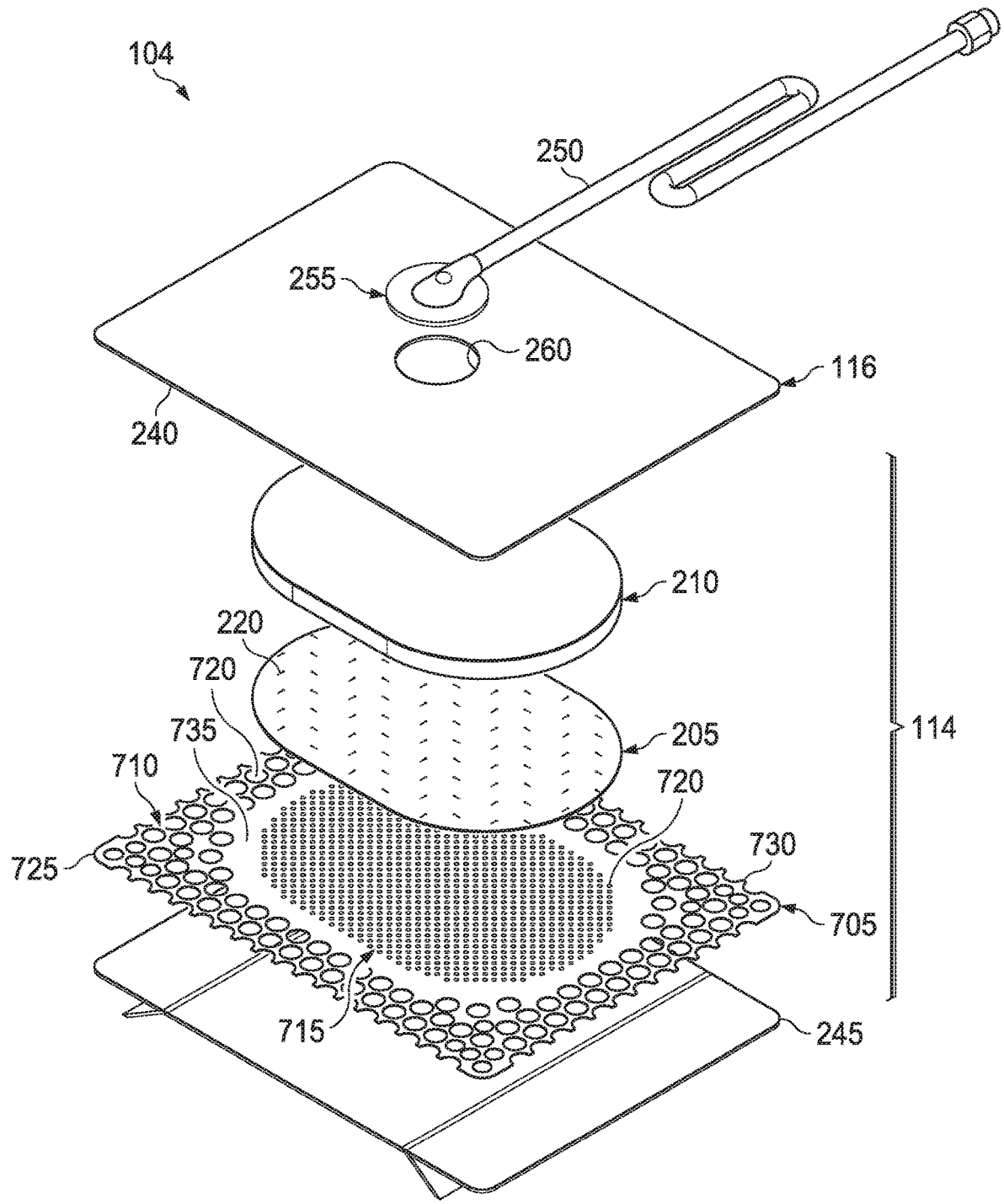
FIG. 7 is an assembly view of another example of a dressing, illustrating additional details that may be associated with some example embodiment of the therapy system of FIG. 1.

FIG. 7 is an assembly view of another example of the dressing 104 of FIG. 1, illustrating additional details that may be associated with some embodiments in which the tissue interface 114 may comprise additional layers. In the example of FIG. 7, the tissue interface 114 comprises a third layer 705 in addition to the second layer 210 and the first layer 205. In some embodiments, the third layer 705 may be adjacent to the first layer 205 opposite the second layer 210. The third layer 705 may also be bonded to the first layer 205 in some embodiments.

The third layer 705 may comprise or consist essentially of a sealing layer formed from a soft, pliable material suitable for providing a fluid seal with a tissue site, and may have a substantially flat surface. For example, the third layer 705 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the third layer 705 may have a thickness between about 200 microns (μm) and about 1000 microns (μm). In some embodiments, the third layer 705 may have a hardness between about 5 Shore OO and about 80 Shore OO. Further, the third layer 705 may be comprised of hydrophobic or hydrophilic materials. For example, the third layer 705 may include a hydrophobic gel.

In some embodiments, the third layer 705 may be a hydrophobic-coated material. For example, the third layer 705 may be formed by coating a spaced material, such as, for example, woven, nonwoven, molded, or extruded mesh with a hydrophobic material. The hydrophobic material for the coating may be a soft silicone, for example.

The third layer 705 may have a periphery 710 surrounding or around an interior portion 715, and apertures 720 disposed through the periphery 710 and the interior portion 715. The interior portion 230 may correspond to a surface area of the second layer 210 in some examples. The third layer 705 may also have corners 725 and edges 730. The corners 725 and the edges 730 may be part of the periphery 710. The third layer 705 may have an interior border 735 around the interior portion 715, disposed between the interior portion 715 and the periphery 710. The interior border 735 may be substantially free of the apertures 720, as illustrated in the example of FIG. 3. In some examples, as illustrated in FIG. 3, the interior portion 715 may be symmetrical and centrally disposed in the third layer 705.

The apertures 720 may be formed by cutting or by application of local RF or ultrasonic energy, for example, or by other suitable techniques for forming an opening. The apertures 720 may have a uniform distribution pattern, or may be randomly distributed on the third layer 705. The apertures 720 in the third layer 705 may have many shapes, including circles, squares, stars, ovals, polygons, slits, complex curves, rectilinear shapes, triangles, for example, or may have some combination of such shapes.

Each of the apertures 720 may have uniform or similar geometric properties. For example, in some embodiments, each of the apertures 720 may be circular apertures, having substantially the same diameter. In some embodiments, the diameter of each of the apertures 720 may be between about 1 millimeter to about 50 millimeters. In other embodiments, the diameter of each of the apertures 720 may be between about 1 millimeter to about 20 millimeters.

In other embodiments, geometric properties of the apertures 720 may vary. For example, the diameter of the apertures 720 may vary depending on the position of the apertures 720 in the third layer 705, as illustrated in FIG. 7. In some embodiments, the diameter of the apertures 720 in the periphery 710 of the third layer 705 may be larger than the diameter of the apertures 720 in the interior portion 715 of the third layer 705. For example, in some embodiments, the apertures 720 disposed in the periphery 710 may have a diameter between about 9.8 millimeters to about 10.2 millimeters. In some embodiments, the apertures 720 disposed in the corners 725 may have a diameter between about 7.75 millimeters to about 8.75 millimeters. In some embodiments, the apertures 720 disposed in the interior portion 715 may have a diameter between about 1.8 millimeters to about 2.2 millimeters.

At least one of the apertures 720 in the periphery 710 of the third layer 705 may be positioned at the edges 730 of the periphery 710, and may have an interior cut open or exposed at the edges 730 that is in fluid communication in a lateral direction with the edges 730. The lateral direction may refer to a direction toward the edges 730 and in the same plane as the third layer 705. As shown in the example of FIG. 7, the apertures 720 in the periphery 710 may be positioned proximate to or at the edges 730 and in fluid communication in a lateral direction with the edges 730. The apertures 720 positioned proximate to or at the edges 730 may be spaced substantially equidistant around the periphery 710. Alternatively, the spacing of the apertures 720 proximate to or at the edges 730 may be irregular.

As illustrated in the example of FIG. 7, in some embodiments, the release liner 245 may be attached to or positioned adjacent to the third layer 705 to protect the adhesive 240 prior to use. In some embodiments, the release liner 245 may have a surface texture that may be imprinted on an adjacent layer, such as the third layer 705. Further, a release agent may be disposed on a side of the release liner 245 that is configured to contact the third layer 705.

Individual components of the dressing 104 in the example of FIG. 7 may be bonded or otherwise secured to one another with a solvent or non-solvent adhesive, or with thermal welding, for example, without adversely affecting fluid management. Further, the first layer 205 or the second layer 210 may be coupled to the border 735 of the third layer 705 in any suitable manner, such as with a weld or an adhesive, for example.

The cover 116, the second layer 210, the first layer 205, the third layer 705, or various combinations may be assembled before application or in situ. For example, the cover 116 may be laminated to the second layer 210, and the first layer 205 may be laminated to the second layer 210 opposite the cover 116 in some embodiments. The third layer 705 may also be coupled to the first layer 205 opposite the second layer 210 in some embodiments. In some embodiments, one or more layers of the tissue interface 114 may coextensive. For example, the first layer 205, the third layer 705, or both may be cut flush with the edge of the second layer 210, exposing the edge of the second layer 210, as illustrated in the embodiment of FIG. 7. In other embodiments, the first layer 205, the third layer 705, or both may overlap the edge of the second layer 210. In some embodiments, the dressing 104 may be provided as a single, composite dressing. For example, the third layer 705 may be coupled to the cover 116 to enclose the second layer 210 and the first layer 205, wherein the third layer 705 is configured to face a tissue site. Additionally or alternatively, the first layer 205, the third layer 705, or both may be disposed on both sides of the second layer 210 and bonded together to enclose the second layer 210.

Figure 8:
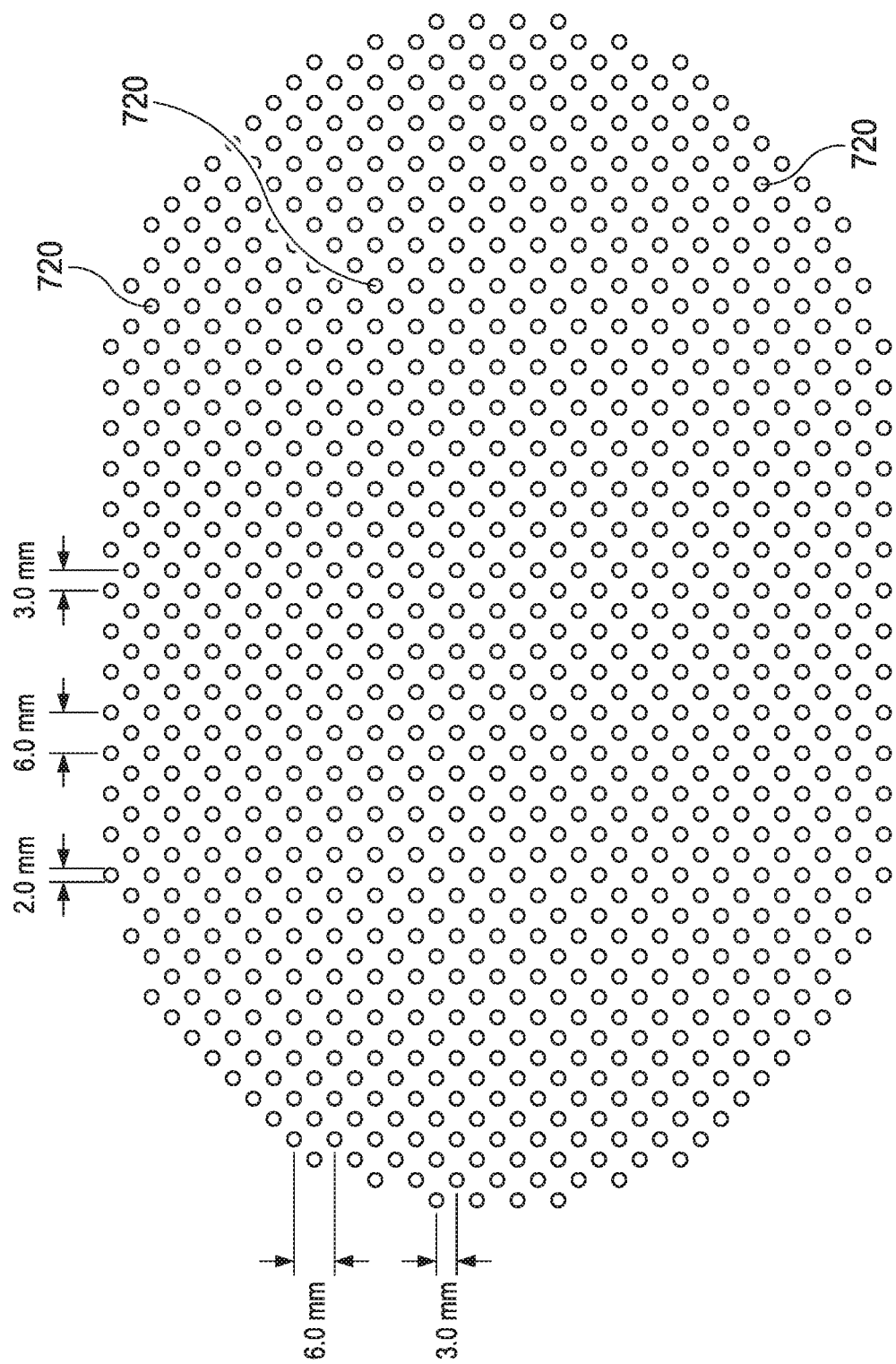
FIG. 8 is a schematic view of an example configuration of apertures in a layer that may be associated with some embodiments of the dressing of FIG. 7.

FIG. 8 is a schematic view of an example configuration of the apertures 720, illustrating additional details that may be associated with some embodiments of the third layer 705. In some embodiments, the apertures 720 illustrated in FIG. 8 may be associated only with the interior portion 715. In the example of FIG. 8, the apertures 720 are generally circular and have a diameter of about 2 millimeters. FIG. 8 also illustrates an example of a uniform distribution pattern of the apertures 720 in the interior portion 715. In FIG. 8, the apertures 720 are distributed across the interior portion 715 in a grid of parallel rows and columns. Within each row and column, the apertures 720 may be equidistant from each other, as illustrated in the example of FIG. 8. FIG. 8 illustrates one example configuration that may be particularly suitable for many applications, in which the apertures 720 are spaced about 6 millimeters apart along each row and column, with a 3 millimeter offset.

Figure 9:
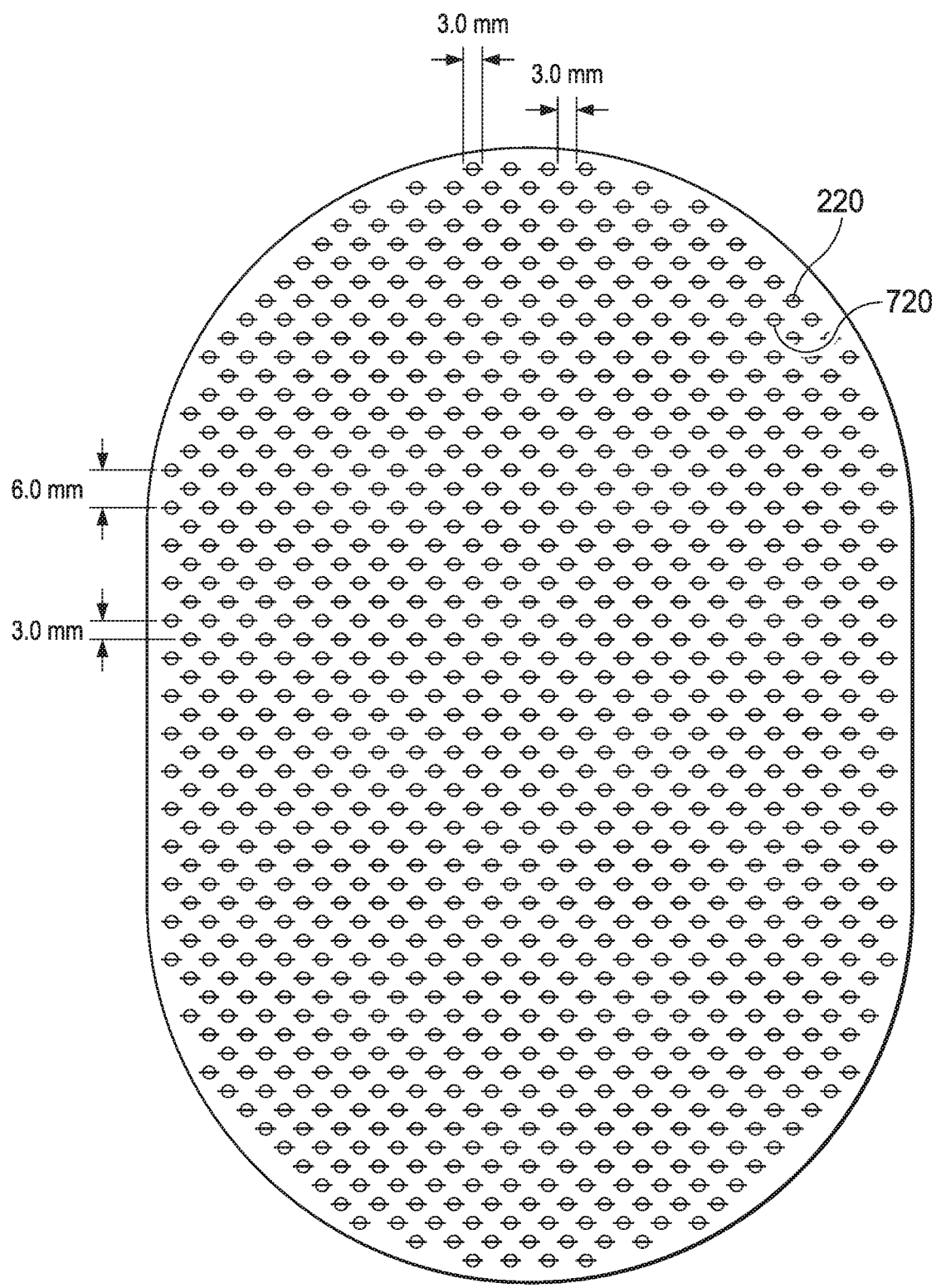
FIG. 9 is a schematic view of the example layer of FIG. 8 overlaid on the example layer of FIG. 3.

FIG. 9 is a schematic view of the example third layer 705 of FIG. 8 overlaid on the first layer 205 of FIG. 3, illustrating additional details that may be associated with some example embodiments of the tissue interface 114. For example, as illustrated in FIG. 9, the fluid restrictions 220 may be aligned, overlapping, in registration with, or otherwise fluidly coupled to the apertures 720 in some embodiments. In some embodiments, one or more of the fluid restrictions 220 may be registered with the apertures 720 only in the interior portion 715, or only partially registered with the apertures 720. The fluid restrictions 220 in the example of FIG. 9 are generally configured so that each of the fluid restrictions 220 is registered with only one of the apertures 720. In other examples, one or more of the fluid restrictions 220 may be registered with more than one of the apertures 720. For example, any one or more of the fluid restrictions 220 may be a perforation or a fenestration that extends across two or more of the apertures 720. Additionally or alternatively, one or more of the fluid restrictions 220 may not be registered with any of the apertures 720.

As illustrated in the example of FIG. 9, the apertures 720 may be sized to expose a portion of the first layer 205, the fluid restrictions 220, or both through the third layer 705. In some embodiments, one or more of the apertures 720 may be sized to expose more than one of the fluid restrictions 220. For example, some or all of the apertures 720 may be sized to expose two or three of the fluid restrictions 220. In some examples, the length of each of the fluid restrictions 220 may be substantially equal to the diameter of each of the apertures 720. More generally, the average dimensions of the fluid restrictions 220 are substantially similar to the average dimensions of the apertures 720. For example, the apertures 720 may be elliptical in some embodiments, and the length of each of the fluid restrictions 220 may be substantially equal to the major axis or the minor axis. In some embodiments, though, the dimensions of the fluid restrictions 220 may exceed the dimensions of the apertures 720, and the size of the apertures 720 may limit the effective size of the fluid restrictions 220 exposed to the lower surface of the dressing 104.

Figure 10:
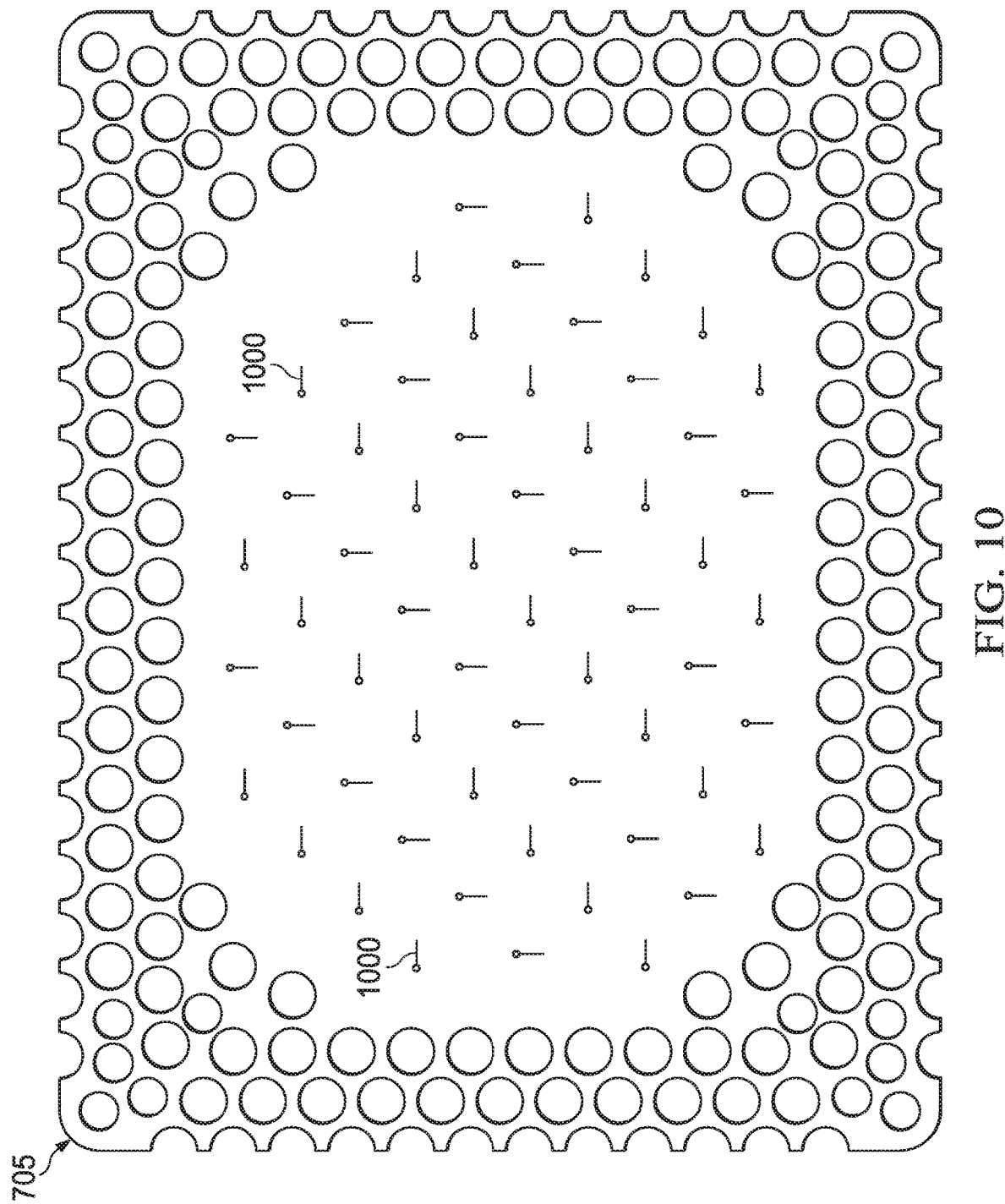
FIG. 10 is a schematic view of another example configuration of fluid restrictions that may be associated with some embodiments of a dressing in the therapy system of FIG. 1.

FIG. 10 is a schematic view of another example of the third layer 705, illustrating additional details that may be associated with some embodiments. As shown in the example of FIG. 10, the third layer 705 may have one or more fluid restrictions, such as valves 1000, instead of or in addition to the apertures 720 in the interior portion 715. The valves 1000 may be elastomeric. In some embodiments in which the third layer 705 includes one or more of the valves 705, the first layer 205 may be omitted. For example, in some embodiments, the tissue interface 114 may consist essentially of the second layer 210 and the third layer 705 of FIG. 10 with the valves 705 disposed in the interior portion 415.

Figure 11:
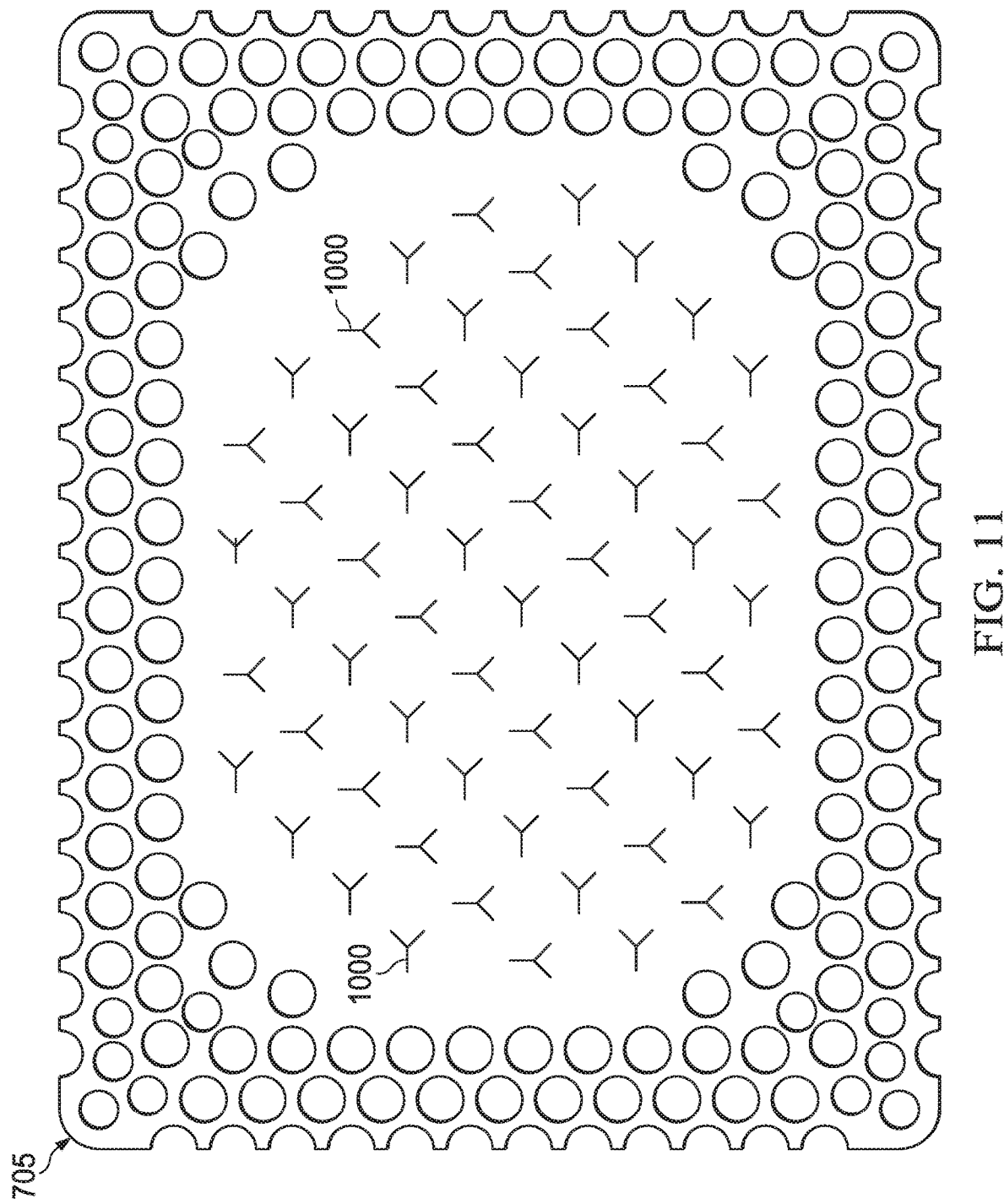
FIG. 11 and FIG. 12 illustrate other example configurations of fluid restrictions that may be associated with some embodiments of the dressing of FIG. 2 or FIG. 4.
Figure 12:
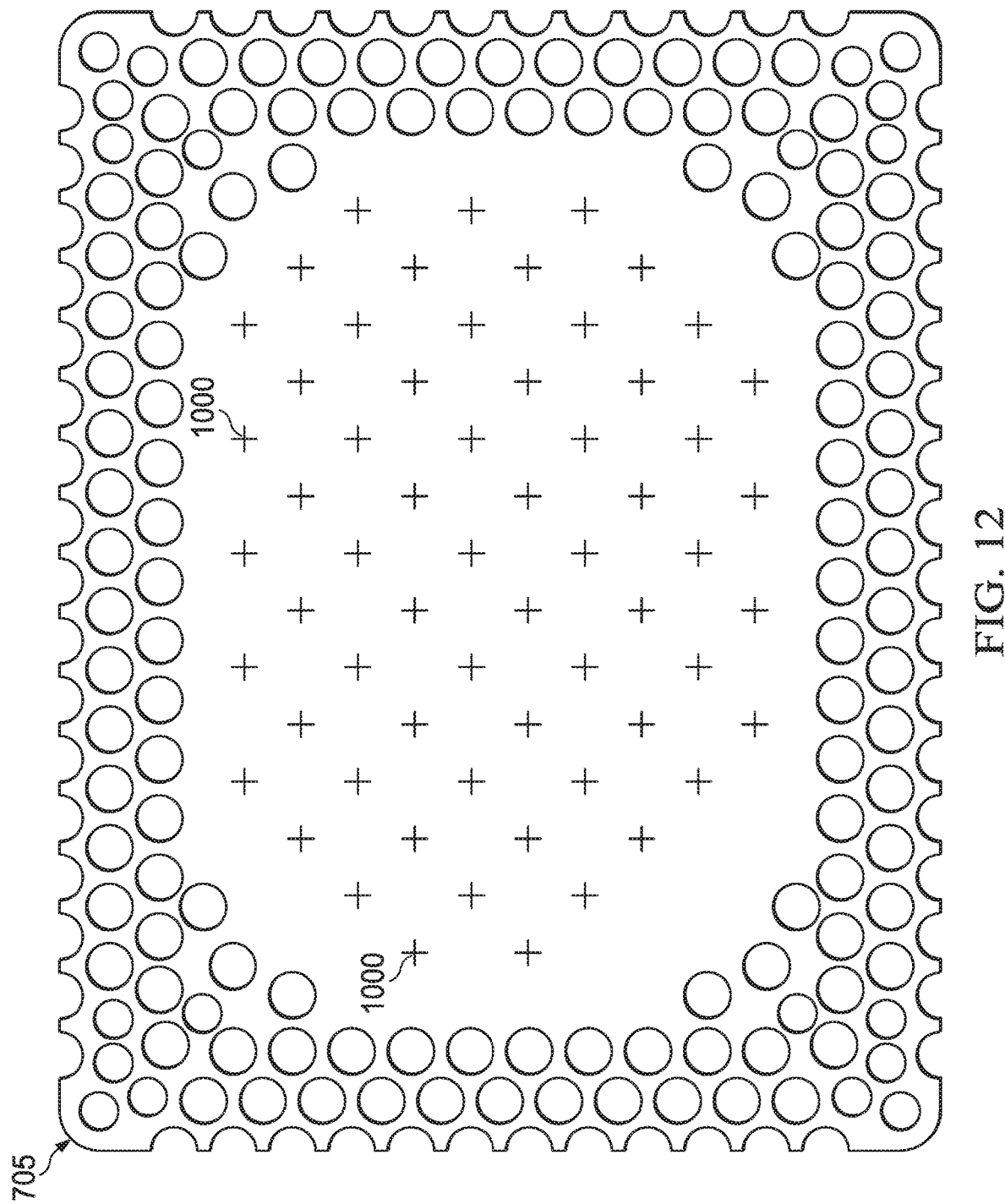

FIG. 11 and FIG. 12 illustrate other example configurations of the valves 1000, in which the valves 1000 each generally comprise a combination of intersecting slits or cross-slits. In some embodiments, shown in FIG. 11, the valves 1000 generally have a "Y" shape. In some embodiments, shown in FIG. 12, the valves 1000 generally have a cross or plus shape.

Figure 13:
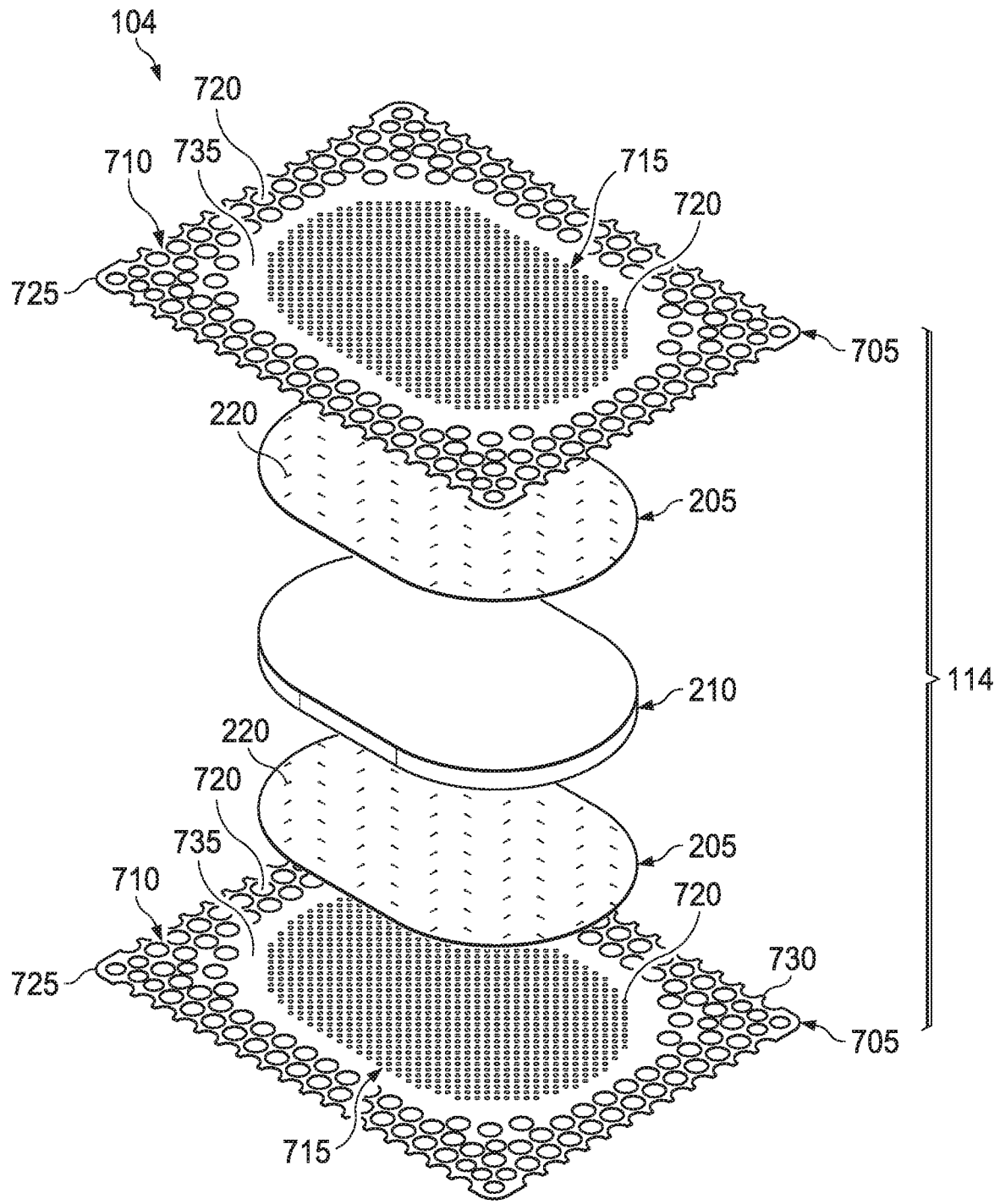
FIG. 13 is an assembly view illustrating an example of a tissue interface that may be associated with some embodiments of the therapy system of FIG. 1.

FIG. 13 is an assembly view of another example of the tissue interface 114 of FIG. 1. In the example of FIG. 13, the first layer 205 is disposed adjacent to two sides of the second layer 210. In some embodiments, for example, the first layer 205 may be laminated or otherwise mechanically bonded to two sides of the second layer 210. Additionally or alternatively, the third layer 705 may be disposed adjacent to one or more sides of the first layer 205, or may be disposed adjacent to the second layer 210. In some embodiments, the third layer 705 may form a sleeve or envelope around the first layer 205, the second layer 210, or both.

In use, the release liner 245 (if included) may be removed to expose the third layer 705, which may be placed within, over, on, or otherwise proximate to a tissue site, particularly a surface tissue site and adjacent epidermis. The third layer 705 and the first layer 205 may be interposed between the second layer 210 and the tissue site, which can substantially reduce or eliminate adverse interaction with the second layer 210. For example, the third layer 705 may be placed over a surface wound (including edges of the wound) and undamaged epidermis to prevent direct contact with the second layer 210. In some applications, the interior portion 715 of the third layer 705 may be positioned adjacent to, proximate to, or covering a tissue site. In some applications, at least some portion of the first layer 205, the fluid restrictions 220, or both may be exposed to a tissue site through the third layer 705. The periphery 710 of the third layer 705 may be positioned adjacent to or proximate to tissue around or surrounding the tissue site. The third layer 705 may be sufficiently tacky to hold the dressing 104 in position, while also allowing the dressing 104 to be removed or re-positioned without trauma to the tissue site.

Removing the release liner 245 can also expose the adhesive 240 and the cover 116 may be attached to an attachment surface, such as epidermis peripheral to a tissue site, around the second layer 210 and the first layer 205. For example, the adhesive 240 may be in fluid communication with an attachment surface through the apertures 420 in at least the periphery 710 of the third layer 705. The adhesive 240 may also be in fluid communication with the edges 730 through the apertures 720 exposed at the edges 730.

Once the dressing 104 is in the desired position, the adhesive 240 may be pressed through the apertures 720 to bond the dressing 104 to the attachment surface. The apertures 720 at the edges 730 may permit the adhesive 240 to flow around the edges 730 for enhancing the adhesion of the edges 730 to an attachment surface.

In some embodiments, apertures or holes in the third layer 705 may be sized to control the amount of the adhesive 240 in fluid communication with the apertures 720. For a given geometry of the corners 725, the relative sizes of the apertures 720 may be configured to maximize the surface area of the adhesive 240 exposed and in fluid communication through the apertures 720 at the corners 725. For example, as shown in FIG. 3, the edges 730 may intersect at substantially a right angle, or about 90 degrees, to define the corners 725. In some embodiments, the corners 725 may have a radius of about 10 millimeters. Further, in some embodiments, three of the apertures 720 having a diameter between about 7.75 millimeters to about 8.75 millimeters may be positioned in a triangular configuration at the corners 725 to maximize the exposed surface area for the adhesive 240. In other embodiments, the size and number of the apertures 720 in the corners 725 may be adjusted as necessary, depending on the chosen geometry of the corners 725, to maximize the exposed surface area of the adhesive 240. Further, the apertures 720 at the corners 725 may be fully housed within the third layer 705, substantially precluding fluid communication in a lateral direction exterior to the corners 725. The apertures 720 at the corners 725 being fully housed within the third layer 705 may substantially preclude fluid communication of the adhesive 240 exterior to the corners 725, and may provide improved handling of the dressing 104 during deployment at a tissue site. Further, the exterior of the corners 725 being substantially free of the adhesive 240 may increase the flexibility of the corners 725 to enhance comfort.

In some embodiments, the bond strength of the adhesive 240 may vary in different locations of the dressing 104. For example, the adhesive 240 may have lower bond strength in locations adjacent to the third layer 705 where the apertures 720 are relatively larger, and may have a higher bond strength where the apertures 720 are smaller. Adhesive 240 with lower bond strength in combination with larger apertures 720 may provide a bond comparable to adhesive 240 with higher bond strength in locations having smaller apertures 720.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the third layer 705 to enhance the movement and proliferation of epithelial cells at a tissue site and reduce the likelihood of granulation tissue in-growth.

Further, the dressing 104 may permit re-application or re-positioning to reduce or eliminate leaks, which can be caused by creases and other discontinuities in the dressing 104 or a tissue site. The ability to rectify leaks may increase the reliability of the therapy and reduce power consumption in some embodiments.

Thus, the dressing 104 can provide a sealed therapeutic environment proximate to a tissue site, substantially isolated from the external environment, and the negative-pressure source 102 can reduce the pressure in the sealed therapeutic environment. The third layer 705 may provide an effective and reliable seal against challenging anatomical surfaces, such as an elbow or heel, at and around a tissue site. Further, the dressing 104 may permit re-application or re-positioning, to correct air leaks caused by creases and other discontinuities in the dressing 104, for example. The ability to rectify leaks may increase the efficacy of the therapy and reduce power consumption in some embodiments.

If not already configured, the dressing interface 255 may be disposed over the aperture 260 and attached to the cover 116. The fluid conductor 250 may be fluidly coupled to the dressing interface 255 and to the negative-pressure source 102.

Negative pressure applied through the tissue interface 114 can create a negative pressure differential across the fluid restrictions 220 in the first layer 205, which can open or expand the fluid restrictions 220. For example, in some embodiments in which the fluid restrictions 220 may comprise substantially closed fenestrations through the first layer 205, a pressure gradient across the fenestrations can strain the adjacent material of the first layer 205 and increase the dimensions of and/or deform the fenestrations to allow liquid movement through them, similar to the operation of a duckbill valve. Opening the fluid restrictions 220 can allow exudate and other liquid movement through the fluid restrictions 220 into the second layer 210 and the container 106. Changes in pressure can also cause the second layer 210 to expand and contract, and the interior border 735 may protect the epidermis from irritation. The first layer 205 and the third layer 705 can also substantially reduce or prevent exposure of tissue to the second layer 210, which can inhibit growth of tissue into the second layer 210. Deformation of the first layer 205 may occur to a greater extent at a central portion than at a peripheral zone, which may allow a greater volume of fluid to flow through the fluid restrictions 220 or the fenestrations 400.

In some embodiments, by mixing the occurrence of the perforations 500 and the fenestrations 400 in the first layer 205, fluid flow may be more readily controlled to increase the flow of fluid in the central zone of the dressing 104, while restricting fluid back flow. The higher valving functionality of the peripheral zone, which is more likely to cover a periwound or intact skin, may reduce fluid reflux and the risk of maceration. The tendency of a higher flow and/or lower pressure drop over the central zone of the dressing may encourage fluid to be drawn away from the dressing perimeter. In some embodiments the perforations and the fenestrations may reduce a risk of fluid arriving at and/or lingering at a periwound or intact skin zone. The dressings may also be more efficient at delivering instillation fluid to the central portion of the dressing and wound, and restricting fluid flow to the periwound area. If the negative-pressure source 102 is removed or turned off, the pressure differential across the fluid restrictions 220 can dissipate, allowing the fluid restrictions 220 to close and prevent exudate or other liquid from returning to the tissue site through the first layer 205.

In some applications, a filler may also be disposed between a tissue site and the third layer 705. For example, if the tissue site is a surface wound, a wound filler may be applied interior to the periwound, and the third layer 705 may be disposed over the periwound and the wound filler. In some embodiments, the filler may be a manifold, such as an open-cell foam. The filler may comprise or consist essentially of the same material as the second layer 210 in some embodiments.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the first layer 205, which can open the fluid restrictions 220 to allow the instillation solution or other fluid to be distributed to a tissue site.

Figure 14:
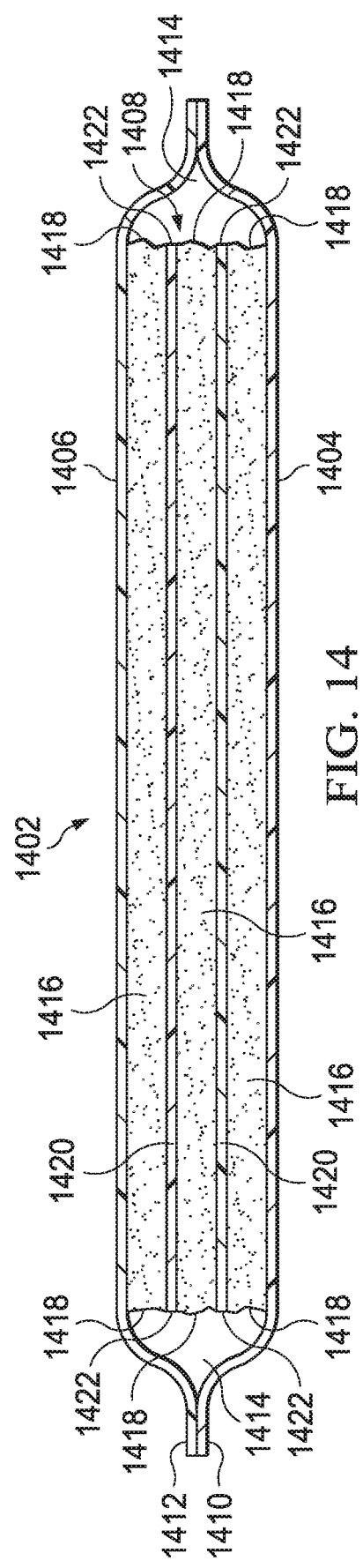
FIG. 14 is a schematic section view of an example manifold that may be associated with some embodiments of the dressing of FIG. 1.

FIG. 14 is a schematic section view of an example manifold that may be associated with some embodiments of the second layer 210. As illustrated in the example of FIG. 14, the manifold may be a fluid management assembly 1402, which may include a first wicking layer 1404, a second wicking layer 1406, and optionally an absorbent 1408. The absorbent 1408 may be positioned between the first wicking layer 1404 and the second wicking layer 1406. The first wicking layer 1404 may have a grain structure (not shown) adapted to wick fluid along a surface of the first wicking layer 1404. Similarly, the second wicking layer 1406 may have a grain structure (not shown) adapted to wick fluid along a surface of the second wicking layer 1406. For example, the first wicking layer 1404 and the second wicking layer 1406 may wick or otherwise transport fluid in a lateral direction along the surfaces of the first wicking layer 1404 and the second wicking layer 1406, respectively. Fluid may be transported in this manner with or without application of reduced pressure. The surfaces of the first wicking layer 1404 and the second wicking layer 1406 may be normal relative to the thickness of each of the first wicking layer 1404 and the second wicking layer 1406. The wicking of fluid along the first wicking layer 1404 and the second wicking layer 1406 may enhance the distribution of the fluid over a surface area of the absorbent 1408, which may increase absorbent efficiency and resist fluid blockages. Fluid blockages may be caused by, for example, fluid pooling in particular location in the absorbent 1408 rather than being distributed more uniformly across the absorbent 1408. A laminate combination of the first wicking layer 1404, the second wicking layer 1406, and the absorbent 1408 may be adapted to maintain an open structure and resist blockage.

A peripheral portion 1410 of the first wicking layer 1404 may be coupled to a peripheral portion 1412 of the second wicking layer 1406 to define a wicking enclosure 1414. In some exemplary embodiments, the wicking enclosure 1414 may surround or otherwise envelope the absorbent 1408 between the first wicking layer 1404 and the second wicking layer 1406.

The fluid management assembly 1402 may include, without limitation, any suitable number of wicking layers as desired for treating a particular tissue site. Additionally or alternatively, some embodiments of the absorbent 1408 may comprise or consist essentially of a plurality of absorbent layers 1416 between the first wicking layer 1404 and the second wicking layer 1406. Further, as depicted in FIG. 14, at least one intermediate wicking layer 1420 may be disposed between the absorbent layers 1416.

Sides 1418 of the absorbent layers 1416 may remain in fluid communication with one another for enhancing efficiency. Similarly, in the embodiment of FIG. 14, sides 1422 of the intermediate wicking layer 1420 may remain in fluid communication with one another and with the sides 1418 of the absorbent layers 1416. Further, including additional absorbent layers 1416 may increase the absorbent mass of the fluid management assembly 1402 and generally provide greater fluid capacity. For a given absorbent mass, multiple light coat-weight absorbent layers 1416 may be utilized rather than a single heavy coat-weight absorbent layer 1416 to provide a greater absorbent surface area for further enhancing the absorbent efficiency.

In some embodiments, the absorbent 1408 may comprise or consist of a hydrophilic material or other absorbent material. Materials suitable for the absorbent 1408 may include Luquafleece® material, Texsus FP2326, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the first wicking layer 1404 and the second wicking layer 1406 may include any material having a grain structure capable of wicking fluid, such as Libeltex TDL2 80 gsm.

The fluid management assembly 1402 may be a pre-laminated structure manufactured at a single location or simply individual layers of material stacked upon one another. Individual layers of the fluid management assembly 1402 may be bonded or otherwise secured to one another without adversely affecting fluid management by, for example, utilizing a solvent or non-solvent adhesive, or by thermal welding.

Figure 15:
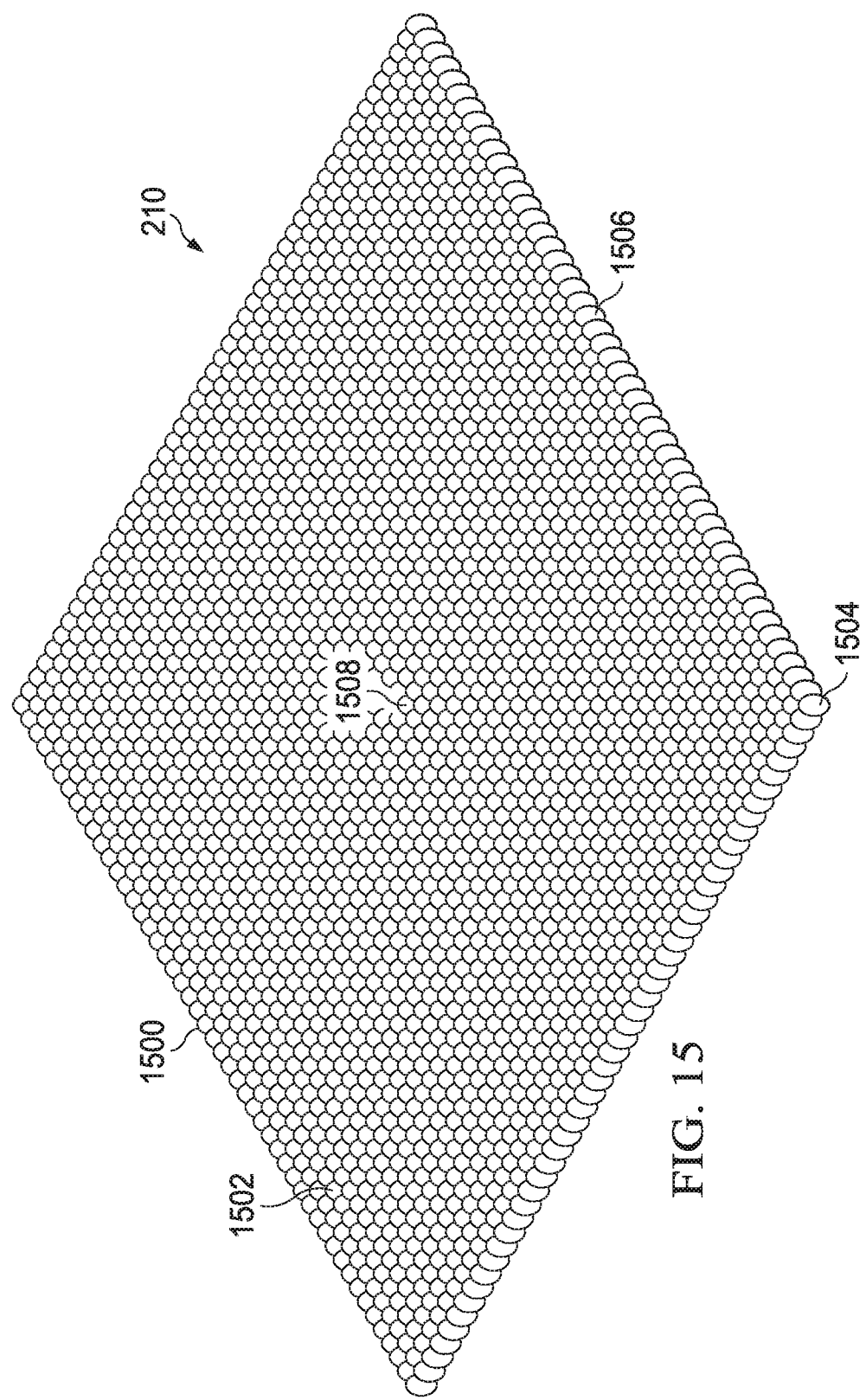
FIG. 15 is a perspective view of an example manifold that may be associated with some embodiments of the dressing of FIG. 1.

FIG. 15 is a perspective view of an example manifold that may be associated with some embodiments of the second layer 210. As illustrated in the example of FIG. 15, the manifold may be a polymer mesh 1500, which may include an array of interconnected ovules 1502 having a truncated ellipsoidal shape. The array of interconnected ovules may include corner ovules 1504, edge ovules 1506, and optionally but preferably at least one central ovule 1508. The array may contain about 50 rows and about 50 columns, but it should be understood that the array may be of any reasonable size and may comprise any number of rows and any number of columns sufficient to assist in treating a tissue site.

In some embodiments, the interconnected ovules may be polymeric, such as comprised of a polyolefin, a polyester, a polyamide, a polystyrene, a polydiolefin, a polyacrylonitrile, a polysiloxane, or a copolymer or combination thereof. In certain embodiments, the interconnected ovules may be non-adherent to a tissue site. In some embodiments, each of the interconnected ovules has a surface hardness from about 0 Shore A to about 25 Shore A. In some embodiments, the upper surface, the lower surface, or both, of the array of interconnected ovules may exhibit a hardness from about 0 Shore A to about 25 Shore A. In some embodiments not shown in the figures, the upper surface, the lower surface, or both, of the array of interconnected ovules may include a coating disposed thereon that exhibits a hardness of at least 55 Shore A. In embodiments when a coating is present, the coating may be comprised of a cellulosic material, a polyester, a polyamide, a polycarbonate, a perhalogenated polyolefin, an aramid, a polybenzimidazole, a polysulfone, or a copolymer, combination, or cross-linked gel thereof.

In some embodiments, at least a portion of the interconnected ovules may include one or more grooves on an outer surface of each ovule that extend at least partially in a direction of its longest principal axis. In embodiments where one or more grooves are present, each groove may have an average depth no more than 30% of a diameter of each interconnected ovule along a principal axis direction other than the longest principal axis. Additionally or alternatively, at least a portion of the interconnected ovules may have an external texture, whether in relief or counter-relief, which may be systematic or random, such as texture patterns commercially available from Standex Int'l. Ltd. of London, England.

It can be desirable, in some embodiments, for portions of the ellipsoidal surfaces of the interconnected ovules forming the upper surface of the array, the lower surface of the array, or both, to protrude above/below portions defining the fluid pathways through the array. Without being bound by theory, it is believed that one or more of the sizes of, the shapes of, and the component materials making up the interconnected ovules and defining the fluid pathways therebetween may be tailored to allow negative pressure to be communicated across the array, such as through the fluid pathways without complete collapse under applied negative pressure.

The second layer 1500 may be made using any viable technique, such as compression or injection molding using one or more pre-made forms. If more than one pre-made form is used, the forms can be combined thereafter, such as by melt-joining or an equivalent technique, to form a single as-synthesized wound filler. However, continuous or semi-continuous manufacture may be employed as an alternative to molding, for example by using a rotary die that can vary its orifice appropriately to allow for extrusion of the complex surfaces of the wound filler materials.

In some embodiments, the second layer 1500 may optionally comprise one or more additional materials. Such optional components may include, for example, active materials such as preservatives, stabilizing agents, plasticizers, matrix strengthening materials, dyestuffs, and combinations thereof. Such optional components may additionally or alternatively include passive materials, for example in situations when ex vivo detection may be important, such as a sufficient amount of magnetic, metal, or ceramic material to allow ready ex vivo detection, such as via an x-ray or MRI apparatus. Additionally or alternatively, the second layer 1500 may comprise one or more additional active materials, for example, antimicrobial agents that may be effective to aid in tissue healing. Non-limiting examples of such active materials may include non-steroidal anti-inflammatory drugs such as acetaminophen, steroids, antimicrobial agents such as penicillins or streptomycins, antiseptics such as chlorhexidine, growth factors such as fibroblast growth factor or platelet derived growth factor, and other well-known therapeutic agents, alone or in combination. If present, such active materials may typically be included at any effective level that show therapeutic efficacy, while preferably not being at such a high level as to significantly counteract any critical or desired physical, chemical, or biological property of the wound filler. Depending upon the therapeutic goal(s), the active material(s) may be loaded at a level of from about 10 wppm to about 10 wt % of the layer(s) in which it(they) is(are) present, for example, from about 50 wppm to about 5 wt % or from about 100 wppm to about 1 wt %.

In various embodiments, the second layer 210 may comprise or consist essentially of the manifold 1500. Additionally or alternatively, the manifold 1500 may be combined with other manifold structures, other functional layers, or both in the second layer 210.

FIG. 16 is a partial view of another example of a manifold that may be associated with some embodiments of the second layer 210. For example, FIG. 16 illustrates a manifold having protrusions 1604 extending from a substrate 1606. As illustrated in the example of FIG. 16, the shape of the protrusions 1604 may be substantially cylindrical. Alternatively, the cross-sectional shape of the protrusions 1604 may be square, rectangular, triangular, polygonal, elliptical, or any other suitable shape. The protrusions 1604 may be tapered or of uniform cross-sectional area throughout.

The height, H, of the protrusions 1604 is preferably between about 0.1 and 5.0 millimeters, and more preferably about 2 millimeters. The width, W, of each protrusion is between about 0.1 and 2.0 millimeters, and more preferably about 0.25 to 0.5 millimeters. The width of the protrusions 1604 may equal that of the diameter since the cross-sectional shape of each protrusion 1604 is circular. If the protrusions 1604 are square in cross-sectional shape, the width of the protrusions 1604 are an edge length of the square. For other cross-sectional shapes, the width is the average of the longest lateral distance through the centroid of the cross section and the shortest lateral distance through the centroid of the cross section. The lateral, center-to-center spacing between each protrusion 1604 is preferably between about 0.1 and 1.0 millimeters, and more preferably about 0.5 millimeters. The spacing of the protrusions 1604 create distribution channels 1610 through which reduced pressure may be delivered to the tissue site 31 and exudates withdrawn from the tissue site. It is generally preferred that the height of the protrusions 1604 be greater than the width of the protrusions 1604. More specifically, the ratio of height to width, H:W, should be greater than about 1:1, and more preferably greater than about 2:1.

The shape, sizing, and spacing of the protrusions 1604 may vary depending upon the particular tissue site being treated, the type of material from which the protrusions 1604 and backing substrate 1606 are made, and the amount of reduced pressure being applied to the tissue site. For example, for tissue sites that are highly exudating, it may be advantageous to position the protrusions farther apart to maintain adequate distribution channels 1610 between the protrusions 1604. In one embodiment of the present invention, the shape, sizing and spacing of the protrusions 1604 is uniform for a particular second layer 1600. In other embodiments, the shape, sizing, and spacing of the protrusions 1604 may vary. For example, protrusions 1604 having different cross-sectional shapes may be disposed on the backing substrate 41. Similarly, the sizing and spacing of the protrusions 1604 may vary to supply selected portions of the tissue site with more or less reduced pressure.

The presence and sizing of the protrusions 1604 can allow the protrusions 1604 to distribute reduced pressure to the tissue site, but can substantially reduce or prevent new tissue that grows at the tissue site from attaching to the protrusions 1604 of the second layer 1600. By eliminating the pores or cells that are typically used to deliver reduced pressure to a tissue site, new tissue may not be able to wrap around the walls that form the pores or cells. While new tissue may grow into the field of protrusions 1604 and may even wrap around some of the protrusions 1604, the new tissue may not be capable of securing itself to the protrusions 1604 since the base of each protrusion is anchored to the backing substrate 1606.

In various embodiments, the second layer 210 may comprise or consist essentially of a manifold having protrusions 1604. Additionally or alternatively, the protrusions 1604 may be combined with other manifold structures, other functional layers, or both in the second layer 210.

The systems, apparatuses, and methods described herein may provide significant advantages. For example, the dressing 104 is simple to apply without customization or special skills, which can reduce the time to apply and remove the dressing 104. In some embodiments, the dressing 104 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, protection of the peripheral tissue from maceration, protection of the tissue site from shedding materials, and a low-trauma and high-seal bond. In addition, by manifolding pressure through the layers, the wound may be granulated while reducing opportunity for in-growth of granulation tissue into the manifold. These characteristics may be particularly advantageous for surface wounds having moderate depth and medium-to-high levels of exudate. In some embodiments, the dressing 104 may provide macro-stain to edges of a tissue site, and may substantially reduce or prevent maceration of peripheral tissue. Moreover, the dressing 104 may conform to and within a significant wound space.

Some embodiments of the dressing 104 may remain on the tissue site for at least 5 days, and some embodiments may remain for at least 7 days. Antimicrobial agents in the dressing 104 may extend the usable life of the dressing 104 by reducing or eliminating infection risks that may be associated with extended use, particularly use with infected or highly exuding wounds.

Felted foam may allow for a reduced profile of the dressing 104 in some embodiments, which may improve conformability. Using a biopolymer, such as ORC collagen, may additionally impart the benefits of the biopolymer. Some embodiments may allow for fluid to be absorbed at a tissue site, and some embodiments may have a greater area behind the film layers to allow for greater valve movement. In addition, some embodiments may provide a means to reduce biofilm and bacterial build-up within the dressing structure.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context.

Features, elements, and aspects described in the context of some embodiments may also be omitted, combined, or replaced by alternative features serving the same, equivalent, or similar purpose without departing from the scope of the invention defined by the appended claims. For example, one or more of the features of some layers may be combined with features of other layers to provide an equivalent function. Alternatively or additionally, one or more of the fluid restrictions 220 may have shapes similar to shapes described as exemplary for the valves 705. In other examples, the first layer 205, the third layer 705, or some combination of the first layer 205 and the third layer 705 may be coupled to both sides of the second layer 210.

Components may be also be combined or eliminated in various configurations for purposes of sale, manufacture, assembly, or use. For example, in some configurations the dressing 104, the container 106, or both may be separated from other components for manufacture or sale. In other example configurations, components of the dressing 104 may also be manufactured, configured, assembled, or sold independently or as a kit.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
   a first layer having a first side, a second side, and fenestrations including raised edges extending from the first side, wherein the raised edges are configured to be collapsed into contact with each other at rest and to separate in response to a pressure gradient across the first layer;
   a second layer adjacent to the first side, the second layer comprising a manifold and an edge that is positioned flush with an edge of the first layer;
   a cover coupled to the second layer opposite the first layer, the cover comprising a polymer drape; and
   a third layer coupled to the first layer opposite the second layer, the third layer comprising a hydrophobic gel having a plurality of apertures, wherein a length of one or more of the fenestrations exceeds a dimension of at least one of the plurality of apertures, and wherein the plurality of apertures are configured to expose at least a portion of one of the fenestrations and a portion of the first layer around the fenestration to the tissue site.

2. The dressing of claim 1, wherein the first layer is hydrophobic.

3. The dressing of claim 1, wherein:
   the first layer is hydrophobic;
   the manifold is hydrophobic; and
   the first layer is more hydrophobic than the manifold.

4. The dressing of claim 1, wherein the first layer comprises a polymer film having a contact angle with water greater than 90 degrees.

5. The dressing of claim 1, wherein the fenestrations are configured to restrict liquid transfer across the first layer from the first side to the second side.

6. The dressing of claim 1, wherein the first layer is configured to be interposed between the manifold and the tissue site.

7. The dressing of claim 1, wherein the fenestrations are coextensive with the first layer.

8. The dressing of claim 1, wherein the fenestrations are coextensive with the manifold.

9. The dressing of claim 1, wherein the fenestrations are distributed across the first layer in a uniform pattern.

10. The dressing of claim 1, wherein the fenestrations are distributed across the first layer in a grid of parallel rows and columns.

11. The dressing of claim 1, wherein:
    the fenestrations are distributed across the first layer in parallel rows and columns;
    the parallel rows are spaced about 3 millimeters on center; and
    the fenestrations in each of the parallel rows are spaced about 3 millimeters on center.

12. The dressing of claim 1, wherein the first layer has a substantially flat surface.

13. The dressing of claim 1, wherein the fenestrations are asymmetrical.

14. The dressing of claim 1, wherein the first layer is welded to the second layer.

15. The dressing of claim 1, wherein:
    the first layer is hydrophobic; and
    the first layer is welded to the manifold.

16. The dressing of claim 1, wherein the first layer comprises or consists of a polyethylene film or an ethyl methyl acrylate film.

17. The dressing of claim 1, wherein the first layer comprises or consists essentially of a polyethylene film having an area density of less than 30 grams per square meter.

18. The dressing of claim 1, wherein:
    the first layer comprises or consists essentially of a polyethylene film or an ethyl methyl acrylate film; and
    the first layer is welded to the manifold.

19. The dressing of claim 1, wherein:
    the first layer comprises or consists essentially of a polyethylene film or an ethyl methyl acrylate film;
    the manifold comprises polyurethane foam; and
    the first layer is welded to the manifold.

20. The dressing of claim 1, wherein:
    the first layer comprises or consists essentially of a polyethylene film;

the manifold comprises polyurethane foam; and
the polyethylene film is welded to the manifold with a tie layer.

21. The dressing of claim 1, wherein:
the first layer comprises or consists essentially of a polyethylene film laminated to an ethyl methyl acrylate film;
the manifold comprises polyurethane foam; and
the ethyl methyl acrylate film is welded to the manifold.

22. The dressing of claim 1, wherein:
the first layer comprises or consists essentially of a polyethylene film laminated to at least one of a film of polyamide, co-polyesters, ionomers, and acrylics; and
the first layer is welded to the manifold.

23. The dressing of claim 1, further comprising a tie layer between the first layer and the second layer.

24. The dressing of claim 1, wherein the first layer comprises a coating of silicone.

25. The dressing of claim 1, wherein the first layer comprises a coating of fluorocarbons.

26. The dressing of claim 1, wherein the plurality of apertures are in registration with at least some of the fenestrations in the first layer.

27. The dressing of claim 1, wherein one or more of the fenestrations comprises a slot or a slit including a length that exceeds the dimension of at least one of the plurality of apertures such that the slot or the slit overlaps an edge of the at least one of the plurality of apertures.

* * * * *